US012213656B2

(12) United States Patent
Blumenthal

(10) Patent No.: US 12,213,656 B2
(45) Date of Patent: Feb. 4, 2025

(54) BALLOON CLOSURE DEVICE

(71) Applicant: Steven Jay Blumenthal, Cold Springs Harbor, NY (US)

(72) Inventor: Steven Jay Blumenthal, Cold Springs Harbor, NY (US)

( * ) Notice: Subject to any disclaimer, the term of this patent is extended or adjusted under 35 U.S.C. 154(b) by 920 days.

(21) Appl. No.: 17/147,341

(22) Filed: Jan. 12, 2021

(65) Prior Publication Data

US 2021/0204925 A1 Jul. 8, 2021

Related U.S. Application Data

(63) Continuation-in-part of application No. 16/031,141, filed on Jul. 10, 2018, now Pat. No. 10,952,710.

(60) Provisional application No. 62/960,096, filed on Jan. 12, 2020, provisional application No. 62/533,054, filed on Jul. 16, 2017.

(51) Int. Cl.
*A61B 17/00* (2006.01)

(52) U.S. Cl.
CPC ...... *A61B 17/0057* (2013.01); *A61B 2017/00592* (2013.01); *A61B 2017/00619* (2013.01); *A61B 2017/00623* (2013.01); *A61B 2017/00646* (2013.01); *A61B 2017/00672* (2013.01); *A61B 2017/00676* (2013.01)

(58) Field of Classification Search
CPC ...... A61B 17/0057; A61B 2017/00592; A61B 2017/00619; A61B 2017/00623; A61B 2017/00646; A61B 2017/00672; A61B 2017/00676; A61B 2017/00336; A61B 2017/00557; A61B 2017/00654; A61B 2017/00884; A61B 2090/0811; A61B 2017/00637; A61B 17/12109; A61B 2018/00589; A61B 17/34; A61M 25/0102
See application file for complete search history.

(56) References Cited

U.S. PATENT DOCUMENTS

| 4,341,218 | A | * | 7/1982 | U | A61B 17/12136 |
| | | | | | 604/99.04 |
| 5,108,421 | A | | 4/1992 | Fowler | |
| 5,192,302 | A | | 3/1993 | Kensey et al. | |
| 5,222,974 | A | | 6/1993 | Kensey et al. | |
| 5,383,896 | A | * | 1/1995 | Gershony | A61B 17/0057 |
| | | | | | 606/213 |
| 5,413,571 | A | | 5/1995 | Katsaros | |
| 6,048,358 | A | | 4/2000 | Barak | |

(Continued)

*Primary Examiner* — Tan-Uyen T Ho
*Assistant Examiner* — Osama Nemer

(57) ABSTRACT

A puncture sealing system for sealing a vascular puncture comprises an inner member and an outer member comprising a lumen sized and shaped to allow the inner member to slide therein, an occlusion balloon at an outer member distal end, and an inflation lumen that extends from an outer member proximal end to the interior of the occlusion balloon. The occlusion balloon can be inflated by fluid flowing through the outer member inflation lumen so that the occlusion balloon can enable the occlusion of a vascular puncture and contact and apply pressure to a puncture tract extending from the vascular puncture. In one version, the inner member further comprises a vessel locator system. In one version, the puncture sealing system further comprises an obturator slidably receivable within the outer member and having a distal end adapted to at least partially cover the puncture.

20 Claims, 35 Drawing Sheets

(56) References Cited

U.S. PATENT DOCUMENTS

| | | | |
|---|---|---|---|
| 6,071,300 A | 6/2000 | Brenneman | |
| 6,139,556 A | 10/2000 | Kontos | |
| 6,296,657 B1 | 10/2001 | Brucker | |
| 6,371,975 B2 | 7/2002 | Cruise | |
| 6,638,268 B2 * | 10/2003 | Niazi | A61M 25/0662 |
| | | | 604/528 |
| 7,025,776 B1 | 4/2006 | Houser | |
| 7,223,266 B2 * | 5/2007 | Lindenbaum | A61B 18/1492 |
| | | | 606/49 |
| 7,331,979 B2 | 2/2008 | Khosravi et al. | |
| 7,789,893 B2 | 9/2010 | Drasler | |
| 8,088,101 B2 * | 1/2012 | Chang | A61B 17/1604 |
| | | | 604/96.01 |
| 8,444,671 B2 | 5/2013 | Yassinzadeh | |
| 8,758,398 B2 * | 6/2014 | Carley | A61B 17/068 |
| | | | 606/213 |
| 8,814,859 B2 * | 8/2014 | Drasler | A61B 17/0057 |
| | | | 606/41 |
| 9,089,311 B2 * | 7/2015 | Fortson | A61B 17/0057 |
| 9,089,674 B2 * | 7/2015 | Ginn | A61B 17/0057 |
| 10,327,747 B2 * | 6/2019 | Yassinzadeh | A61B 17/0057 |
| 11,766,544 B2 * | 9/2023 | Kojima | A61M 25/10 |
| | | | 604/509 |
| 2002/0072767 A1 | 6/2002 | Zhu | |
| 2002/0133123 A1 * | 9/2002 | Zucker | A61B 17/0057 |
| | | | 604/246 |
| 2003/0055397 A1 | 3/2003 | Zucker | |
| 2003/0125766 A1 | 7/2003 | Ding | |
| 2004/0153060 A1 | 8/2004 | Lindenbaum | |
| 2006/0287674 A1 * | 12/2006 | Ginn | A61B 17/083 |
| | | | 606/221 |
| 2008/0065150 A1 * | 3/2008 | Drasler | A61B 17/0057 |
| | | | 606/213 |
| 2008/0065151 A1 * | 3/2008 | Ginn | A61B 17/0057 |
| | | | 606/213 |
| 2008/0154303 A1 | 6/2008 | Yassinzadeh | |
| 2011/0106148 A1 * | 5/2011 | Ginn | A61B 17/083 |
| | | | 606/213 |

\* cited by examiner

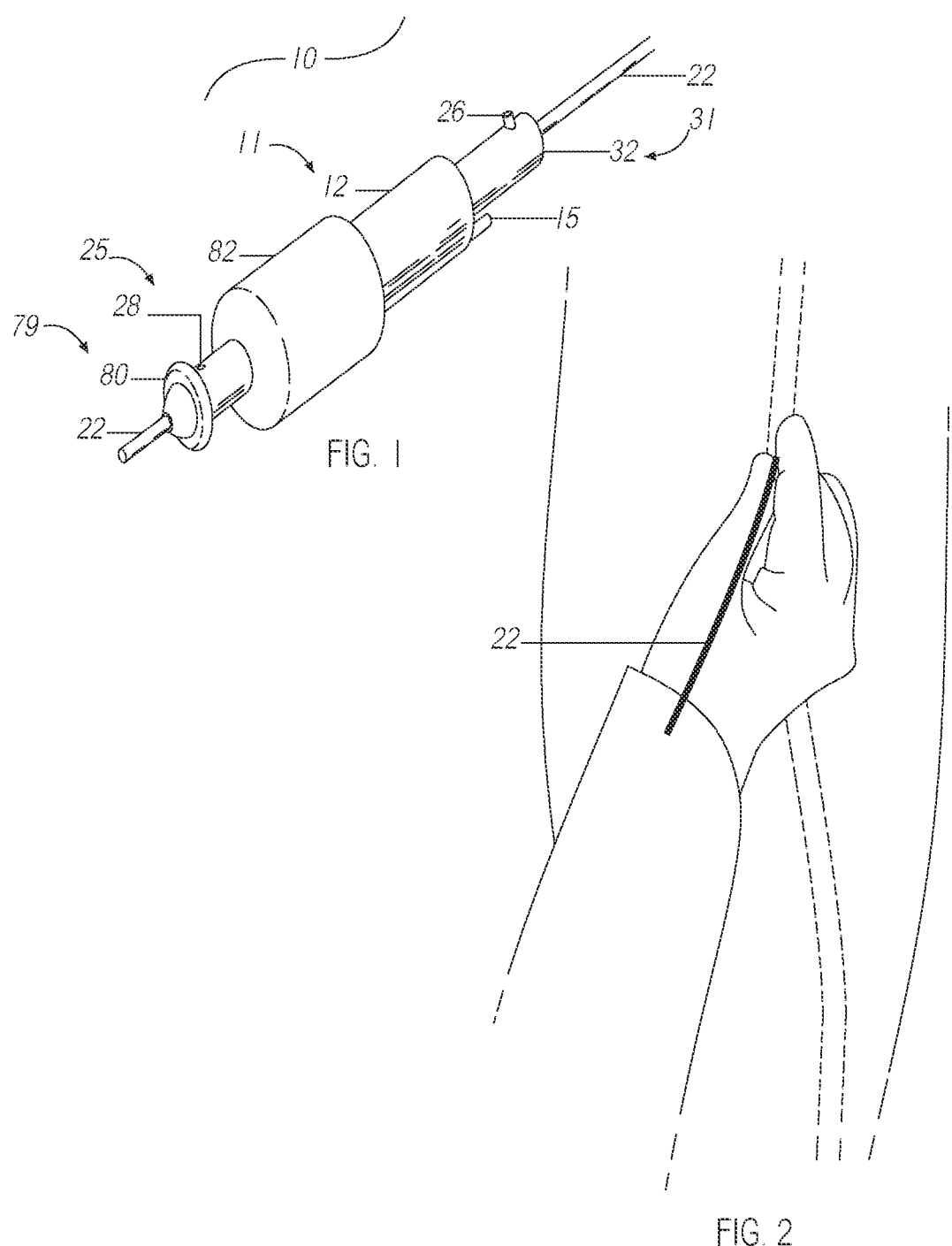

BALLOON CLOSURE DEVICE

PRIORITY

The present application is a Continuation-in-Part of U.S. patent application Ser. No. 16/031,141 filed on Jul. 10, 2018, the entirety of which is incorporated herein by reference, which claims the benefit of domestic priority based on U.S. Patent Application 62/533,054 filed on Jul. 16, 2017, the entirety of which is incorporated herein by reference, and the present application also claims the benefit of domestic priority based on U.S. Provisional Patent Application 62/960,096 filed on Jan. 12, 2020, the entirety of which is incorporated herein by reference.

BACKGROUND

A system and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate introducing various devices into the vessel, while minimizing trauma to the vessel wall and/or minimizing blood loss. Upon completing the procedure, the device (s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient and may require the patient to remain immobilized in the operating room, catheter lab, or holding area. In addition, a risk of hematoma exists from bleeding before hemostasis occurs.

Various systems and methods have been suggested for sealing a percutaneous puncture instead of using external pressure. For example, U.S. Pat. No. 5,108,421 to Fowler discloses a collagen plug that may be delivered into a puncture through tissue. In one embodiment, a catheter is inserted through the puncture into the blood vessel. A balloon on the catheter is expanded and retracted until the balloon is disposed adjacent the puncture at the wall of the vessel. The plug may be advanced into the puncture until the plug contacts the balloon, thereby preventing the plug from entering the vessel. Once the plug is positioned within the puncture, the balloon may be deflated and withdrawn, leaving the plug therein to expand and seal the puncture and/or to promote hemostasis.

Alternatively, U.S. Pat. Nos. 5,192,302 and 5,222,974 issued to Kensey et al. describe a biodegradable collagen plug and rigid anchor that may be delivered through an introducer sheath into a puncture site. The disclosed plug, however, may be difficult to position properly with respect to the vessel, which may be significant since it is generally undesirable to expose the collagen material within the bloodstream where it may float downstream and cause an embolism. In addition, the disclosed plug may not completely occlude the puncture site, resulting in incomplete hemostasis and vascular complications.

U.S. Pat. No. 7,331,979 issued to Khosravi et al. describes a balloon that may be delivered through an introducer sheath into a puncture site. The balloon is withdrawn to seal the puncture, and a hydrogel sealant is introduced into the puncture. The balloon is then removed, relying on the hydrogel sealant to occlude the tissue tract. The sealant may not completely occlude the puncture site or tissue tract, resulting in incomplete hemostasis and vascular complications.

Accordingly, there is a need for an improved system and method for sealing vascular punctures. There is a further need for a system and method for sealing vascular punctures that seals both the puncture and the puncture tract. There is a further need for a system and method for sealing vascular punctures that allows for precise placement of the system at the puncture. There is a further need for a system and method for sealing vascular punctures that allows for hemostasis to be assessed and/or confirmed. When other devices, as noted above, fail to achieve hemostasis, the only option is manual compression. Thus, there is a need for a system and method for sealing vascular punctures where prolonged balloon inflation is localized to the puncture tract with nothing intravascular to impair blood flow. There is a further need for a system and method for sealing punctures that does not require additional manpower or beyond standard supervision, may not be uncomfortable for the patient may be possible for the patient to move or even ambulate with the device inflated and secured in the tissue tract, and/or may be scalable for larger punctures, which may require more prolonged and possibly overnight balloon inflation to achieve hemostasis.

SUMMARY

The present invention satisfies these needs. In one aspect of the invention, an improved puncture sealing system and method is provided.

In another aspect of the invention, a puncture sealing system comprises an inner member with an inflatable member and an outer member with an occlusion balloon, the occlusion balloon enabling occlusion of a puncture and a puncture tract.

In another aspect of the invention, a puncture sealing system comprises an inner member with an inflatable member and an outer member with an occlusion balloon, the occlusion balloon enabling occlusion of a puncture and a puncture tract, the puncture sealing system also comprising a vessel locating system.

In another aspect of the invention, a puncture sealing system comprises an inner member with an inflatable member, an outer member with an occlusion balloon, and an obturator, the occlusion balloon and obturator working in combination to enable occlusion of a puncture and a puncture tract.

In another aspect of the invention, a puncture sealing system comprises an inner member with an inflatable member, an outer member with an occlusion balloon, and an obturator, the occlusion balloon and obturator working in combination to enable occlusion of a puncture and a puncture tract, wherein the puncture sealing system also comprises a hemostasis detection system.

In another aspect of the invention, a puncture sealing system for sealing a vascular puncture comprises an inner member comprising an expandable member at an inner member distal end and an inflation lumen that extends from an inner member proximal end to an interior of the expandable member, wherein the inner member further comprises a vessel locator system comprising a lumen extending from one or more vessel locator distal holes to a vessel locator proximal hole; and an outer member comprising a lumen sized and shaped to allow the inner member to slide therein, an occlusion balloon at an outer member distal end, and an inflation lumen that extends from an outer member proximal end to the interior of the occlusion balloon, wherein the expandable member can be inflated by fluid flowing through the inner member inflation lumen so that the expandable member can inflate in a subcutaneous vessel of a living being, and wherein the occlusion balloon can be inflated by fluid flowing through the outer member inflation lumen so that the occlusion balloon can enable the occlusion of a vascular puncture and contact and apply pressure to a puncture tract extending from the vascular puncture.

In another aspect of the invention, a puncture sealing system for sealing a vascular puncture comprises an inner member comprising an expandable member at an inner member distal end and an inflation lumen that extends from an inner member proximal end to an interior of the expandable member; an outer member comprising a lumen sized and shaped to allow the inner member to slide therein, an occlusion balloon at an outer member distal end, and an inflation lumen that extends from an outer member proximal end to the interior of the occlusion balloon; and an obturator slidably receivable within the outer member following removal of the inner member from the outer member, the obturator comprising a distal end positionable in proximity to the vascular puncture, wherein the expandable member can be inflated by fluid flowing through the inner member inflation lumen so that the expandable member can inflate in a subcutaneous vessel of a living being, wherein the occlusion balloon can then be inflated by fluid flowing through the outer member inflation lumen so that the occlusion balloon can contact and apply pressure to a puncture tract extending from the vascular puncture, wherein the expandable member can then be deflated and the inner member removed from the outer member, and wherein the obturator can then be received within the outer member so that the distal end covers at least a portion of the vascular puncture to enable occlusion of the vascular puncture.

In another aspect of the invention, a method of sealing a vascular puncture comprises providing an inner member comprising an expandable member at an inner member distal end and an outer member comprising an occlusion balloon at an outer member distal end, the outer member having a lumen sized and shaped to allow the inner member to slide therein; advancing an inner member into a subcutaneous vessel through a vascular puncture and positioning the inner member in proximity to the puncture; expanding the expandable member within the subcutaneous vessel; expanding the occlusion balloon so that the occlusion balloon contacts a puncture tract extending from the puncture; deflating the expandable member and removing the inner member from the outer member, whereby the occlusion balloon and the obturator in combination enable the occlusion of the vascular puncture and the puncture tract.

In another aspect of the invention, a method of sealing a vascular puncture comprises providing an inner member comprising an expandable member at an inner member distal end and an outer member comprising an occlusion balloon at an outer member distal end, the outer member having a lumen sized and shaped to allow the inner member to slide therein; advancing an inner member into a subcutaneous vessel through a vascular puncture; expanding the expandable member within the subcutaneous vessel; expanding the occlusion balloon so that the occlusion balloon contacts a puncture tract extending from the puncture; deflating the expandable member and removing the inner member from the outer member; and inserting an obturator into the outer member lumen and covering at least a portion of the puncture with a distal end of the obturator, whereby the occlusion balloon and the obturator in combination enable the occlusion of the vascular puncture and the puncture tract.

In another aspect of the invention, a method of sealing a vascular puncture comprises providing an inner member comprising an expandable member at an inner member distal end and an outer member comprising an occlusion balloon at an outer member distal end, the outer member having a lumen sized and shaped to allow the inner member to slide therein; advancing an inner member into a subcutaneous vessel through a vascular puncture; expanding the expandable member within the subcutaneous vessel; expanding the occlusion balloon so that the occlusion balloon contacts a puncture tract extending from the puncture; deflating the expandable member and removing the inner member from the outer member; inserting an obturator into the outer member lumen and covering at least a portion of the puncture with a distal end of the obturator; and detecting whether or not hemostasis has occurred, whereby the occlusion balloon and the obturator in combination enable the occlusion of the vascular puncture and the puncture tract.

The present invention is directed to a system and methods for sealing a puncture in a body, and, more particularly, to a system and methods for providing temporary or permanent hemostasis within a percutaneous puncture comprising a tract extending from a patient's skin, through tissue, to a blood vessel or other body lumen.

In accordance with the present invention, a system is provided for sealing a puncture through tissue that includes an outer member, an inner member slidably coupled to the outer member, and balloons or other expandable members separately coupled to the distal ends of both the inner and outer members. The inner member also includes a vessel locator.

In accordance with the present invention, a system is provided for sealing a puncture through tissue that includes an outer member and an inner member slidably coupled to the outer member, and balloons or other expandable members separately coupled to the distal ends of both the inner and outer members. The outer member may also include at least one blood detection lumen. The inner member may also include at least one vessel locator. An obturator which may have an expandable member coupled to the distal end of the obturator may also be included. The obturator may replace the inner member after removal of the inner member.

In one embodiment, the outer member may include proximal and distal ends defining a longitudinal axis therebetween, a lumen extending between the proximal and distal ends to accommodate the inner member, and an inflation lumen extending between the proximal and distal ends. The expandable member may be coupled circumferentially to the outer border of a distal end segment of the outer member such that an interior of the expandable member communicates with the inflation lumen. Thus, the expandable member may be expandable from a collapsed state to an expanded state when fluid is introduced into the inflation lumen of the outer member, and consequently into the interior of the expandable member.

The inner member may include proximal and distal ends, and an inflation lumen extending between the proximal and distal ends. The inner member is slidably disposed within the lumen of the outer member. The expandable member may be coupled circumferentially to the outer border of a distal end segment of the inner member such that an interior of the expandable member communicates with the inflation lumen. Similarly, the expandable member may be expandable from a collapsed state to an expanded state when fluid is introduced into the inflation lumen of the inner member, and consequently into the interior of the expandable member.

In one embodiment, the outer member may connect to a hemostatic valve on its proximal end, through which the inner member may pass. Such hemostatic valve may be self-closing or manually closed to essentially lock the outer and inner members together allowing them to move as a unit, or restricting their joint movement as desired.

The outer member may include a port on the proximal end that communicates with the inflation lumen, i.e., for connecting a source of fluid to the lumen. The expandable member, coupled with the outer member, may be expanded, i.e., as fluid is delivered into the lumen, and may be collapsed, i.e., as fluid is withdrawn from the lumen, as may be seen with a balloon. Similarly, the inner member may include a port on the proximal end that communicates with the inflation lumen, i.e., for connecting a source of fluid to the lumen. The expandable member, coupled with the inner member, may be expanded, i.e., as fluid is delivered into the lumen, and may be collapsed, i.e., as fluid is withdrawn from the lumen, as may be seen with a balloon.

The outer member may include at least one blood detection lumen. The blood detection lumen may extend from the proximal end to the inner lumen near the distal end of the outer member. The outer member may include a port on the proximal end that communicates with the blood detection lumen.

The obturator may include an expandable member coupled circumferentially to the outer border of a distal end segment of the obturator. The expandable member may be self-expanding, as may be seen with foam, or expanded with fluid, as may be seen with a balloon.

The system may be referred to as the balloon closure device, the outer member may be referred to as the occlusion catheter, the expandable member coupled to the outer member may be referred to as the occlusion balloon, the inner member may be referred to as the anchor catheter, and the expandable member coupled to the inner member may be referred to as the anchor balloon. The anchor catheter may also include at least one vessel locator near its distal end.

The system may be referred to as the balloon closure device, the outer member may be referred to as the occlusion catheter, the expandable member coupled to the outer member may be referred to as the occlusion balloon, the inner member may be referred to as the anchor catheter, and the expandable member coupled to the inner member may be referred to as the anchor balloon. The anchor catheter may also include a vessel locator at its distal end.

In accordance with an embodiment, a method is provided for sealing a puncture extending through tissue and/or communicating with a body lumen using a system including an occlusion catheter, an anchor/introducer catheter slidably coupled to the occlusion catheter, an occlusion balloon coupled to the distal end of the occlusion catheter, an anchor balloon coupled to the distal end of the anchor catheter, at least one vessel locator near the distal end of the anchor catheter, a blood detection lumen near the distal end of the outer member's inner lumen, and an obturator to replace the anchor catheter after the anchor catheter is removed. This design may avoid the need for a separate introducer sheath, as the anchor catheter may act as the introducer for the occlusion catheter. For example, the body lumen may be a blood vessel, e.g., a femoral, carotid, or other peripheral artery.

The balloon closure device, e.g., an anchor catheter, and occlusion catheter, is arranged for location within a portion of the puncture at a desired position with respect thereto, e.g., the anchor catheter within the vessel and the occlusion catheter within the puncture/tissue tract, to enable the effective sealing of the puncture by the closure device. At least one vessel locator, built into the distal end of the anchor catheter, is arranged for introduction into the puncture to locate the wall of the blood vessel and basically comprises means for extension of the anchor catheter in the puncture tract to a position whereupon blood within the vessel is enabled to flow from the interior of the vessel into the vessel locator for detection thereof.

There may be various possible methods for delivering the balloon closure device into the puncture tract, across the puncture, and into the body lumen, as desired. Optionally, the system may include an elongate tubular member, e.g., an introducer sheath, including proximal and distal ends, and a lumen extending therebetween. The lumen may have sufficient size for receiving the outer member therein when the expandable member is in the collapsed state. In this embodiment, the introducer sheath may be a valved hemostatic peel-away sheath. Using this technique, the existing sheath is exchanged for the peel-away sheath, using techniques known in the art. Whereupon, the balloon closure device may be delivered through the sheath to the desired destination. This method requires a peel-away sheath closely corresponding to the size of the existing sheath.

The balloon closure device may be delivered in fewer steps by designing the anchor catheter to also function as the introducer. In this embodiment, the occlusion catheter lumen may have sufficient size for receiving the anchor catheter/introducer. The anchor catheter/introducer may be advanced distal to the occlusion catheter, and then the two may be secured together using the above mentioned hemostatic valve, allowing the two to be advanced as a unit. Tracking over a guidewire, an adequately stiff and tapered anchor catheter/introducer should be able to easily traverse the puncture tract, and enter the body lumen, with the tethered occlusion catheter advanced to the distal end of the puncture tract. This is similar to advancing a vascular sheath with its introducer, as is known in the art. In the case of a blood vessel or other fluid-filled lumen, the anchor catheter/introducer may have a method, e.g., a vessel locator, to indicate that it has entered the lumen. The anchor catheter may, alternatively, enter the lumen simply by being advanced an adequate distance through the puncture tract, based on the original sheath length.

The above mentioned embodiment, with the anchor catheter nested within the occlusion catheter, may result in a balloon closure device with a larger profile. This may not be an issue when using the device to occlude large diameter puncture holes. However, to occlude smaller diameter puncture holes, it may be preferable to use a tapered dilator/introducer rather than the aforementioned anchor catheter, to be nested within the occlusion catheter. This alternative embodiment may result in a smaller profile device. Such a dilator/introducer may similarly have a distal vessel locator to indicate entry into the blood vessel lumen, but would lack an anchor balloon. Instead, the guide wire may be removed and a simple balloon catheter, as is known in the art, may be advanced through the guide wire lumen, enter the blood vessel and function similarly to the anchor balloon, to be further described below.

Any of the aforementioned embodiments may be used to deliver the balloon closure device with similar subsequent steps as described below. The balloon closure device may be introduced into the puncture with the occlusion and anchor balloons in a collapsed state until the expandable member is disposed within the body lumen. If necessary, for example, the system may be introduced through a lumen of a peel-away introducer sheath or other tubular member previously placed in the puncture. In either embodiment, the anchor catheter may be advanced more distally than the occlusion catheter, to enter the body lumen. Once, intraluminal position is confirmed, fluid may be introduced into the anchor catheter to expand the coupled anchor balloon to an expanded state. The anchor catheter may be at least partially withdrawn from the puncture until the anchor balloon engages tissue at a location where the puncture penetrates a wall of the body lumen, thereby substantially sealing the puncture from the body lumen. While pull-back tension is applied to the anchor balloon that is "anchored" in the body lumen, the occlusion catheter may be advanced distally until it abuts the anchor balloon. The introducer sheath, if required, may be retracted, peeled away, and removed. The occlusion balloon may be expanded against the puncture tract wall while also engaging the tissue contiguous with the puncture on the opposite side thereof from the anchor balloon, effectively occluding the puncture, and puncture tract and preventing dislodgment of the balloon closure device. Next, the anchor balloon may be collapsed, withdrawn from the body lumen through the puncture, withdrawn from the puncture tract, and completely removed. The occlusion balloon is designed to completely seal the puncture and the puncture tract. At this point, the balloon closure device is completely outside the body lumen, with the expanded occlusion balloon adhering to the tissue contiguous with the puncture and the puncture tract, essentially locking the balloon closure device in the puncture tract. Optionally, the occlusion balloon may be coated with a procoagulant material (e.g., Chitosan) to enhance coagulation and hemostasis. A transparent adhesive dressing (e.g., Tegaderm) may be applied to further secure the balloon closure device in place.

Another alternative embodiment may use an anchor catheter with multiple distal vessel locators to precisely position the anchor catheter within the blood vessel lumen, and eliminate the need for an anchor balloon. By using two distal vessel locators offset longitudinally by a short distance, the position of the anchor catheter with respect to the inner surface of the blood vessel, may be precisely determined. The anchor catheter is introduced into the body lumen so that both vessel locators are receiving a blood signal. The anchor catheter may be at least partially withdrawn from the puncture until the blood signal is lost by the more proximal vessel locator, while the blood signal is still maintained by the more distal vessel locator. At that point, the occlusion balloon may be expanded, as previously described above.

Another alternative embodiment may use an occlusion balloon that only expands on the outside of the occlusion catheter, as is known in the art, and does not wrap around at its distal end to the inside of the occlusion catheter. In this embodiment, the occlusion balloon will circumscribe and occlude the perimeter of the puncture but may not occlude the occlusion catheter lumen. In this embodiment, once the anchor catheter or dilator/introducer is removed, an obturator may be inserted into the occlusion catheter lumen and advanced to the end of the occlusion catheter to occlude the lumen and the central portion of the puncture. The obturator may have a balloon or other expandable member, like a medical foam, coupled to the distal end of the obturator. The occlusion balloon in combination with the obturator may enable occlusion of the puncture and the puncture tract.

The anchor catheter anchor balloon may be positioned just distal to the anchor catheter blood vessel locator so that when pull-back tension is applied and the inflated anchor balloon encounters the puncture, slight resistance will be appreciated at the same time that the blood vessel locator will leave the blood vessel lumen and the blood signal will be lost, providing a dual detection mechanism for precisely locating the blood vessel wall. The occlusion balloon may be positioned just proximal to the anchor catheter blood vessel locator, so that the occlusion balloon may be precisely positioned to inflate and enable occlusion without the need for any additional movement of the occlusion catheter.

After an appropriate time interval, depending on the size and nature of the puncture (e.g., artery vs. vein), an assessment of hemostasis may be made, possibly with the patient both at rest and with ambulation. The occlusion catheter may have at least one distal blood detection lumen to detect blood in the occlusion catheter lumen. The obturator may be partially withdrawn from the puncture tract to test the blood detection lumen, and advanced distally again as needed. The occlusion balloon may be collapsed to further assess hemostasis. Once hemostasis is confirmed, the balloon closure device may be completely removed from the puncture tract. After adequate balloon and obturator occlusion, there should be no need for any manual compression.

Other objects and features and many of the attendant advantages of the present invention will become apparent from consideration of the following detailed description taken in conjunction with the accompanying drawings.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

FIG. 1 is a perspective view of an embodiment of a puncture sealing system in accordance with the present invention;

FIG. 2 is a perspective view showing an operator inserting a guide wire into a patient's blood vessel;

DESCRIPTION

Figure 3:
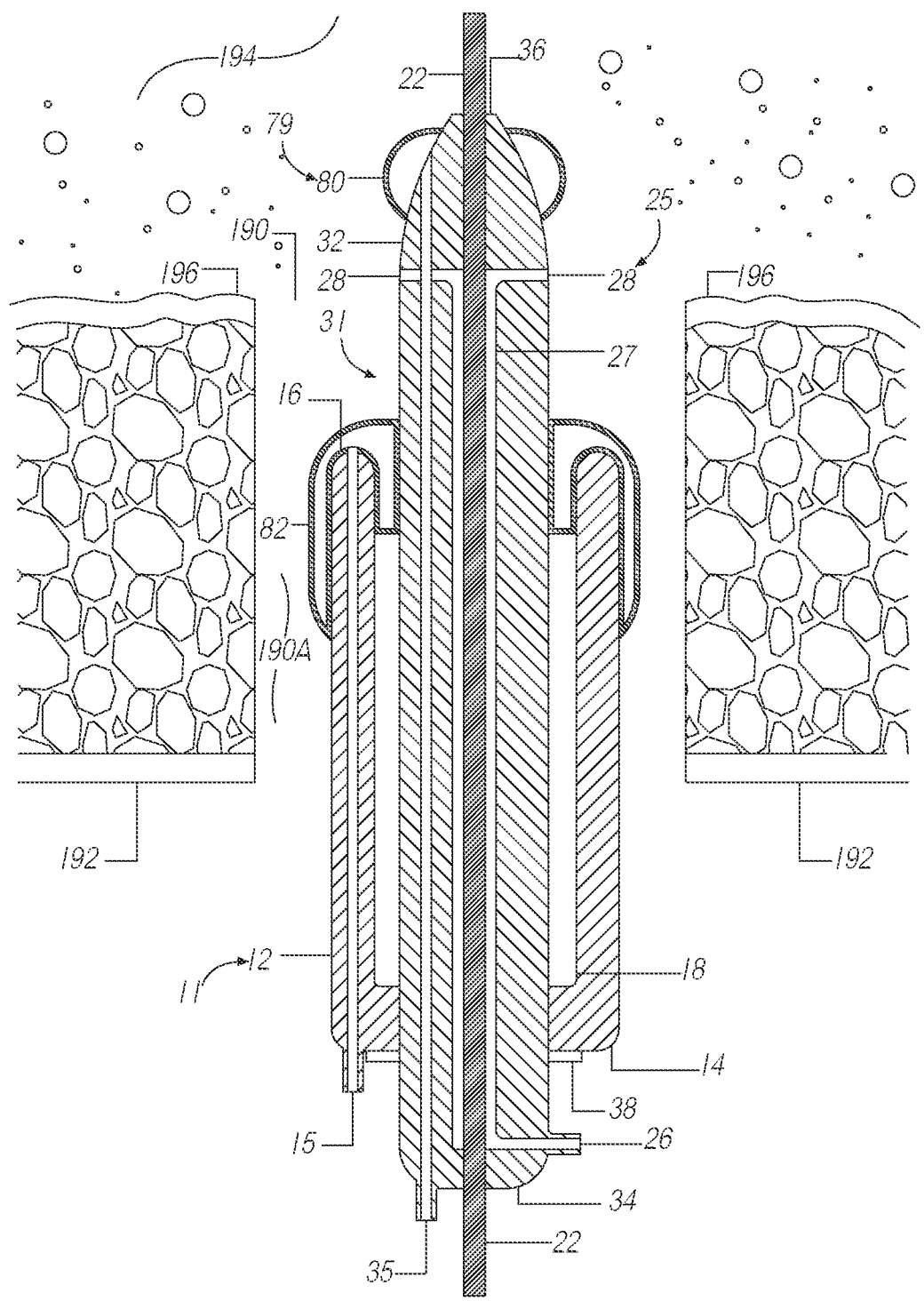
FIG. 3 is a schematic sectional representation of an embodiment of a puncture sealing system in accordance with the present invention.

The present invention relates to a puncture sealing system or balloon closure device and a method of using the puncture sealing system. In particular, the invention relates to a puncture sealing system useful for sealing a puncture and a puncture tract in an improved manner. Although the invention is illustrated and described in the context of being useful for sealing a puncture following a vascular access procedure, the present invention can be used in other ways, as would be readily apparent to those of ordinary skill in the art. Accordingly, the present invention should not be limited just to the examples and embodiments described herein.

Referring now in greater detail to the various figures of the drawings wherein like reference characters refer to like parts. Turning to the drawings, FIGS. 1-12, show an embodiment of a puncture sealing system 10 of the invention. The puncture sealing system 10 is also known as a balloon closure device. By sealing it is meant at least partially sealing, occluding, blocking, coagulating, or the like. The puncture sealing system 10 may be used to seal a vascular puncture 190 extending through tissue and/or communicating with a body lumen. The puncture 190 includes not only the opening in the wall of the vessel but also the puncture tract 190A, i.e., the passageway in the tissue extending from the puncture 190 and at least partially to the skin 192 and formed when the vessel is punctured.

Figure 4:
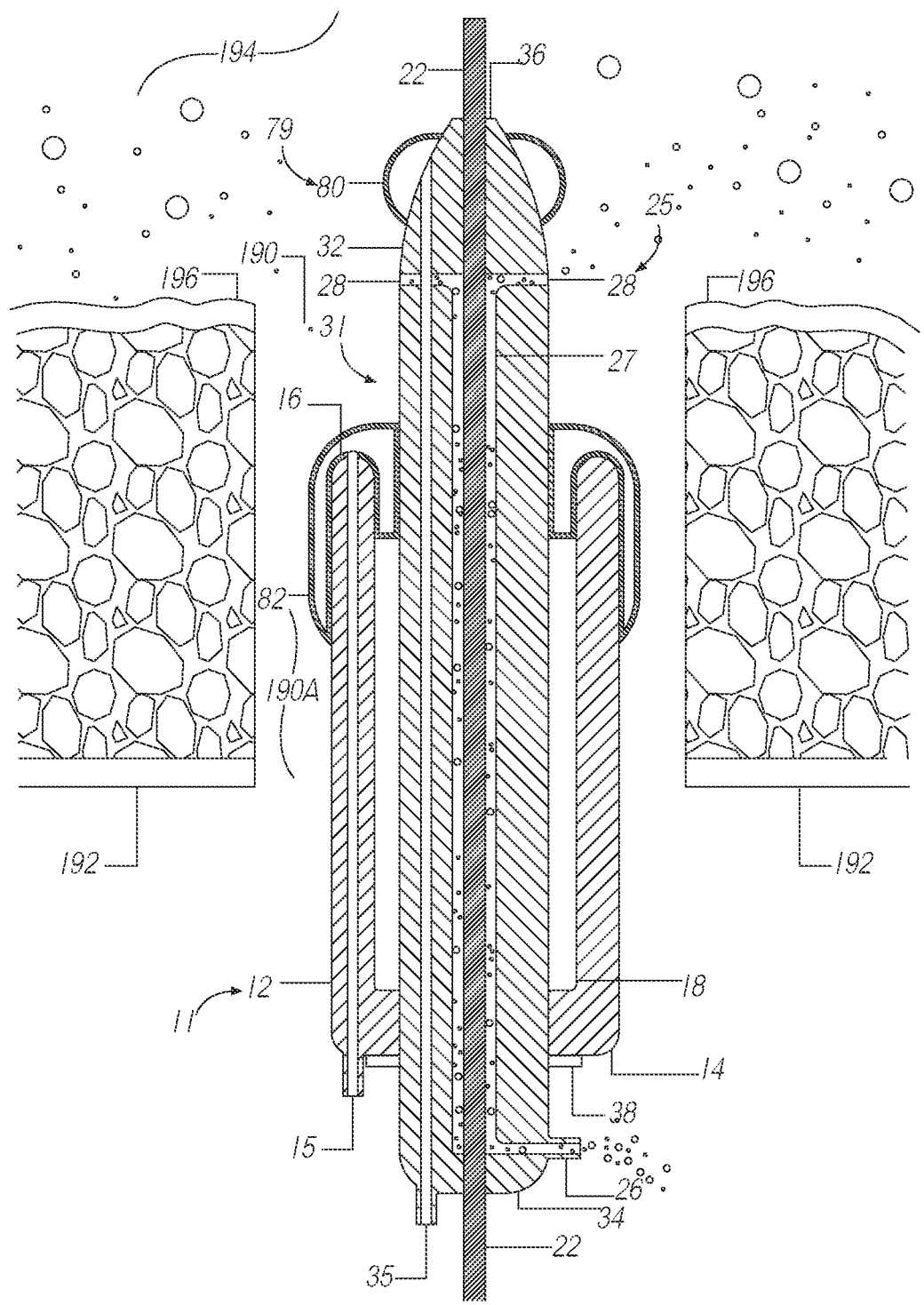
FIG. 4 is a schematic sectional representation of the embodiment of FIG. 3 in use and showing blood flow from the arterial lumen.
Figure 5:
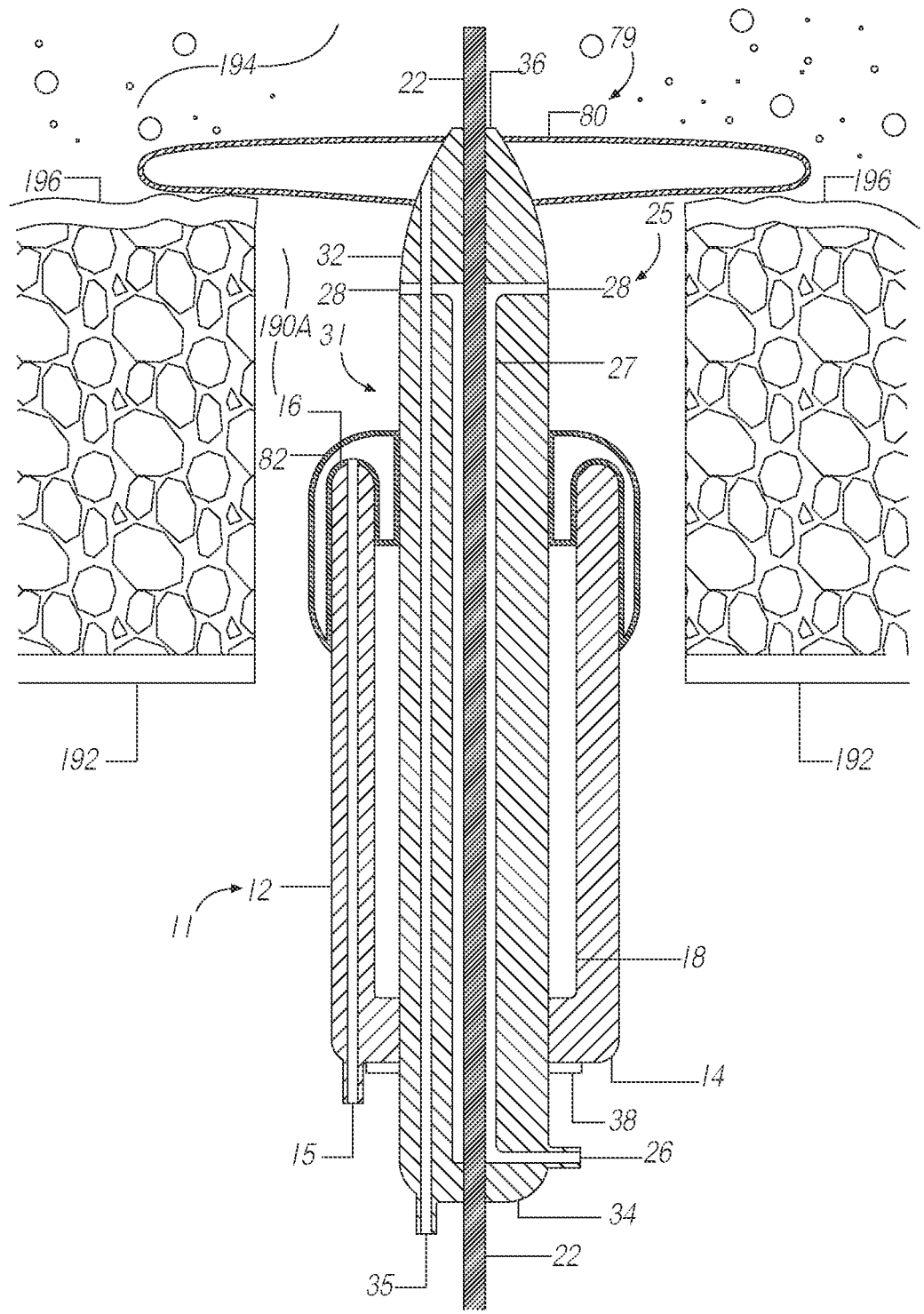
FIG. 5 is a schematic sectional representation of the embodiment of FIG. 3 in use showing an anchor balloon inflated and an anchor catheter/introducer occluding a puncture.
Figure 6:
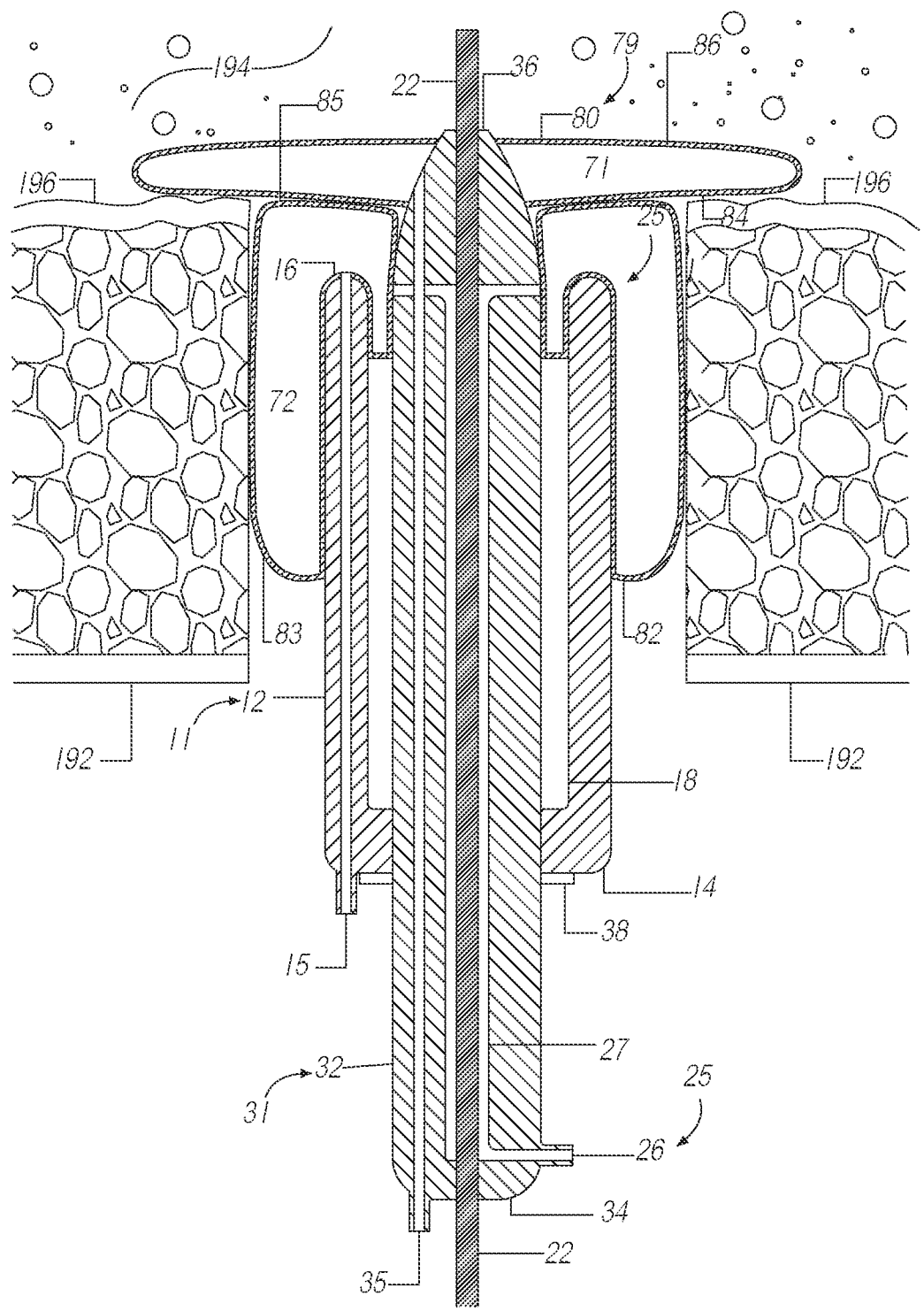
FIG. 6 is a schematic sectional representation of the embodiment of FIG. 3 in use showing an occlusion catheter advanced to the distal end of a puncture tract.
Figure 7:
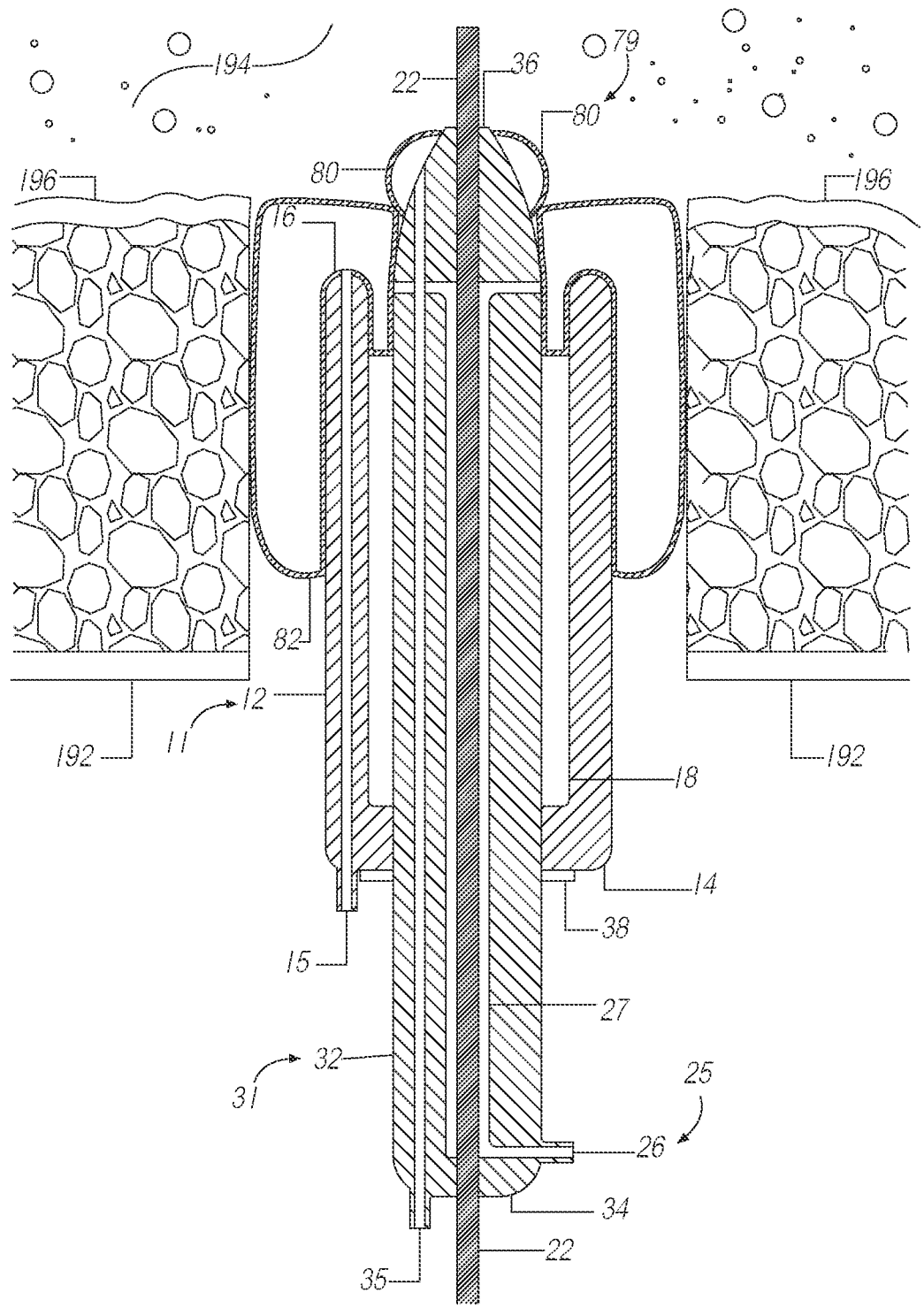
FIG. 7 is a schematic sectional representation of the embodiment of FIG. 3 in use showing an anchor balloon deflated and an inflated occlusion balloon.
Figure 8:
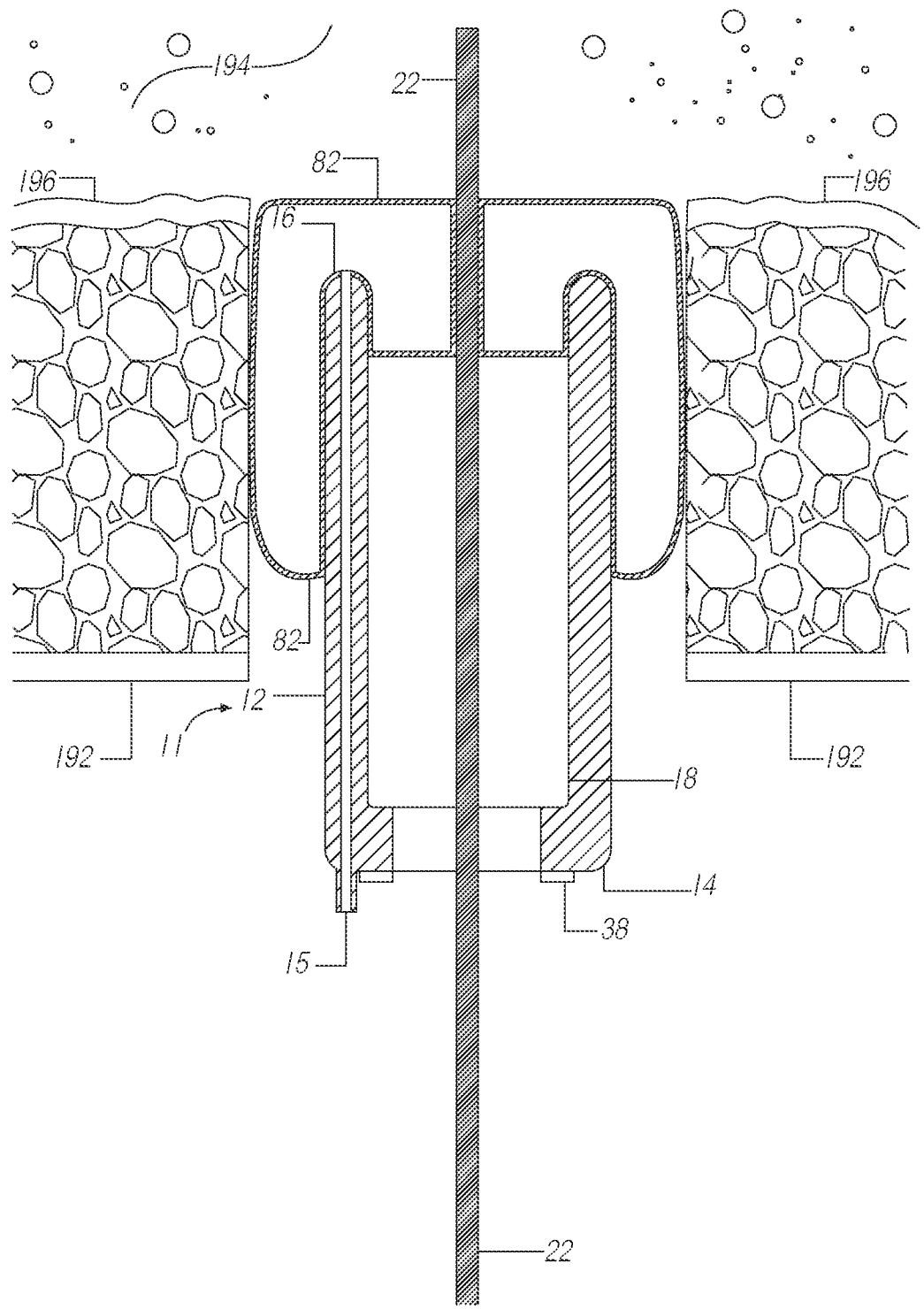
FIG. 8 is a schematic sectional representation of the embodiment of FIG. 3 in use showing an anchor catheter removed and an, occlusion balloon filling the vacated space.
Figure 9:
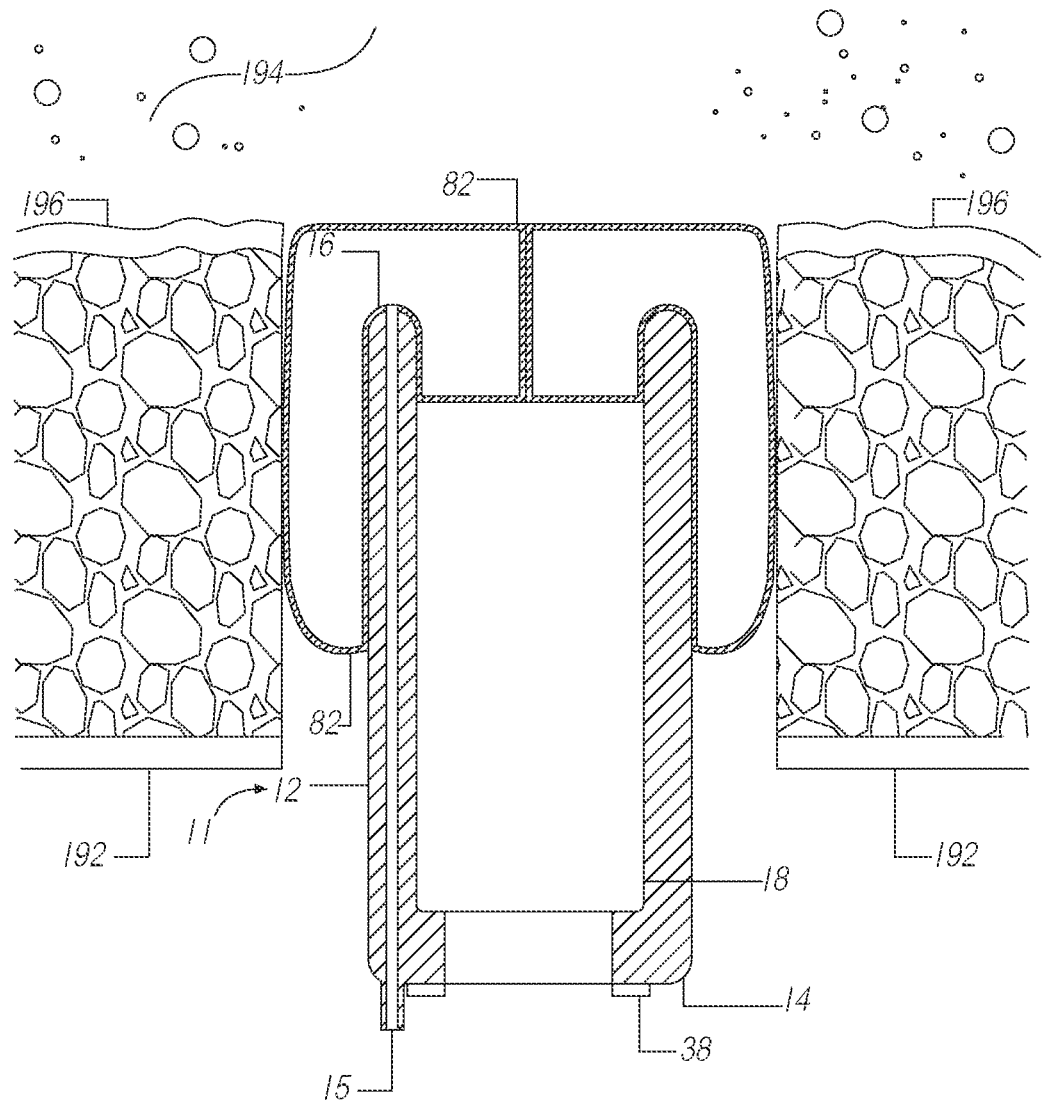
FIG. 9 is a schematic sectional representation of the embodiment of FIG. 3 in use showing a guidewire removed.
Figure 10:
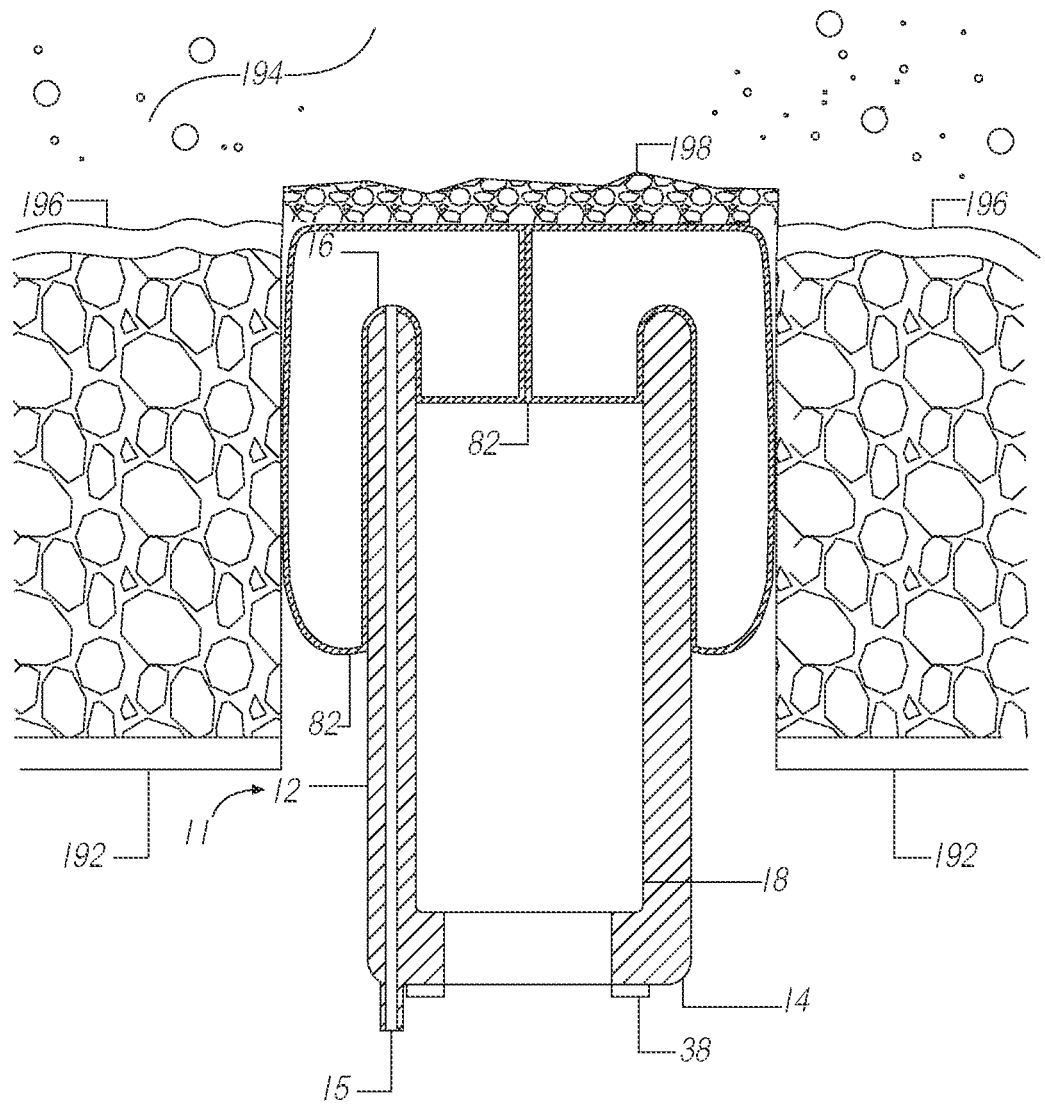
FIG. 10 is a schematic sectional representation of the embodiment of FIG. 3 in use showing a hemostatic layer has formed at a puncture site.
Figure 11:
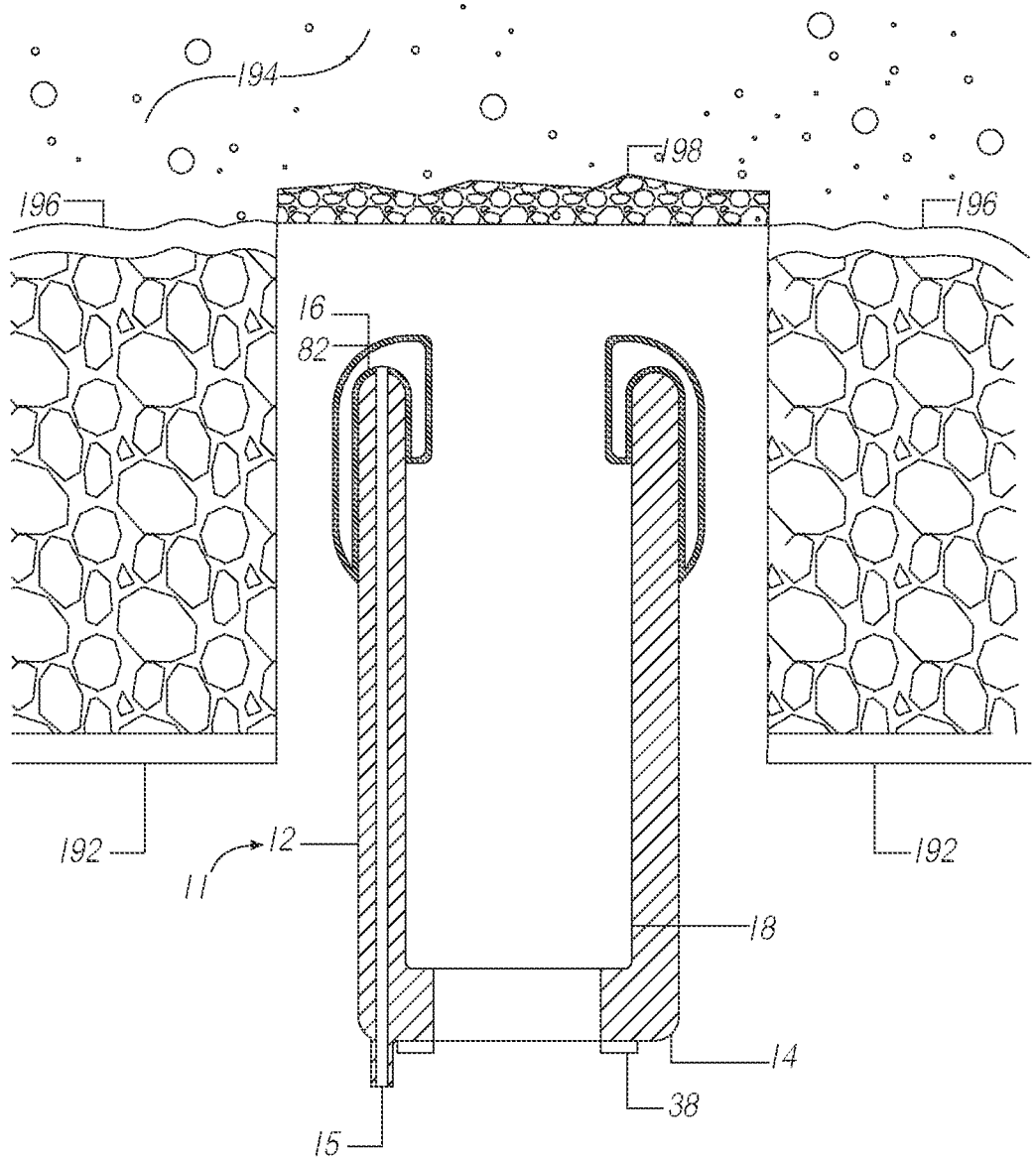
FIG. 11 is a schematic sectional representation of the embodiment of FIG. 3 in use showing an occlusion balloon deflated to assess the stability of a hemostatic layer that has formed at a puncture site.
Figure 12:
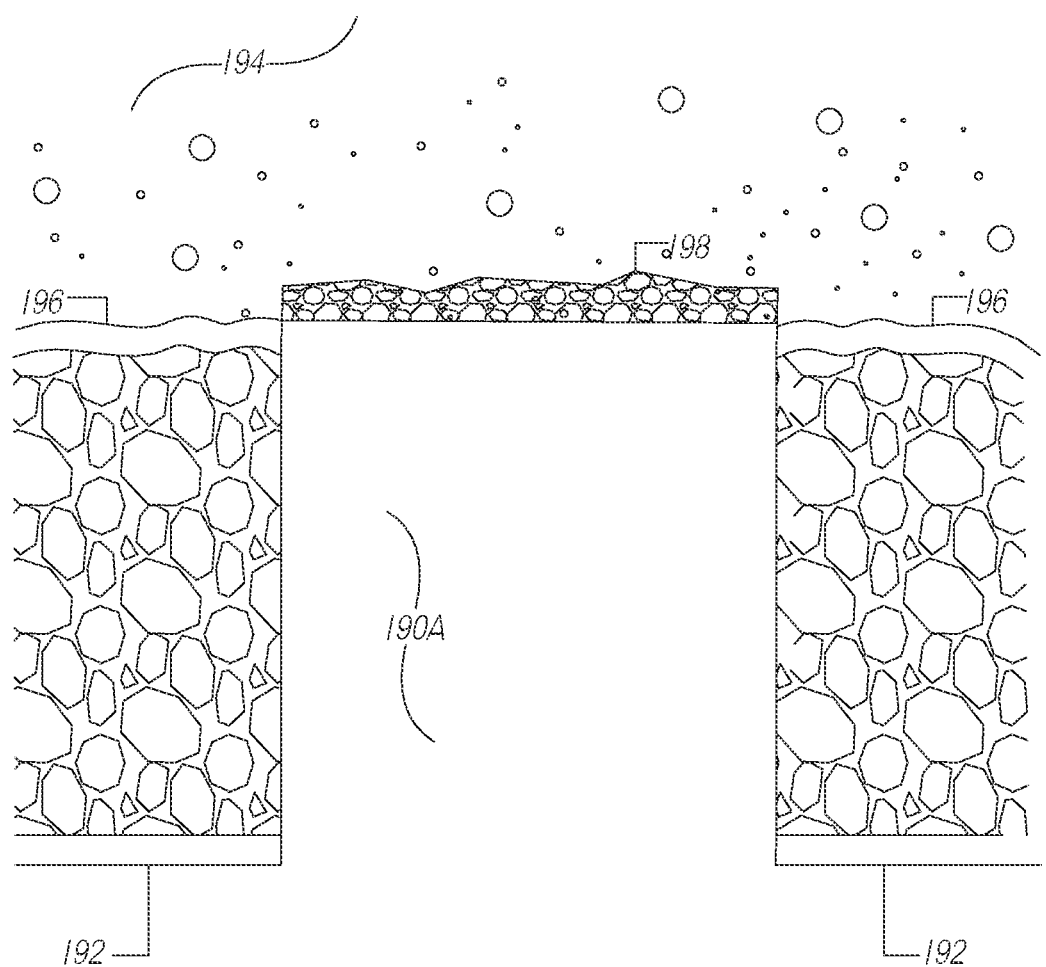
FIG. 12 is a schematic sectional representation of hemostasis confirmed after a balloon closure device has been removed, leaving behind a hemostatic plug.
Figure 13:
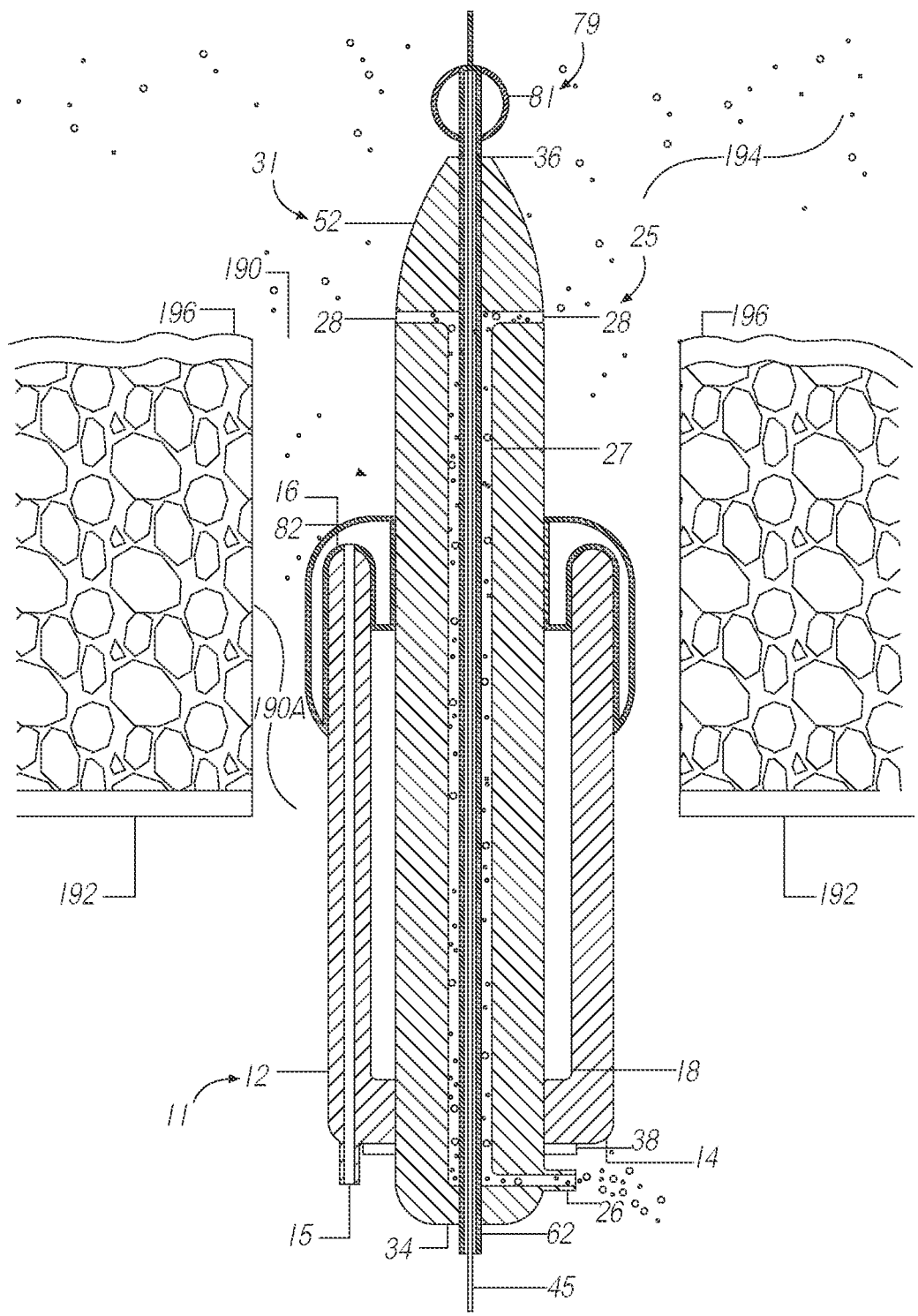
FIG. 13 is a schematic sectional representation of another embodiment of a puncture sealing system in accordance with the present invention.

Briefly, FIG. 1 shows an embodiment of a puncture sealing system 10 in accordance with the present invention. FIG. 2 shows an operator inserting a guide wire 22 into a patient's blood vessel prior to the sealing of the puncture. FIG. 3 shows a puncture sealing system 10 including an outer member 11, such as an occlusion catheter 12, and with an inner member 31, such as an anchor catheter/introducer 32. The anchor catheter/introducer 32 extends into the arterial lumen, and the occlusion catheter 12 resides in the puncture tract 190A. The inner member 31 has an inner member expandable member 79, such as anchor balloon 80, and the outer member 11 has an occlusion balloon 82, both of which are deflated in FIG. 3. FIG. 4 shows the puncture sealing system 10 showing a vessel locator system 25 that demonstrates blood flow from the arterial lumen, confirming the anchor catheter's location in the arterial lumen 194. FIG. 5 shows the anchor balloon 80 inflated and the anchor catheter/introducer 32 pulled back, occluding the puncture 190. FIG. 6 shows the occlusion catheter 12 advanced to a distal end of the puncture tract 190A, abutting the inflated anchor balloon 80, and the occlusion balloon 82 is inflated to occlude the puncture 190 and the puncture tract 190A. FIG. 7 shows the anchor balloon 80 deflated and hemostasis, resulting from the inflated occlusion balloon 82, is assessed. FIG. 8 shows the anchor catheter 32 removed, the occlusion balloon 82 filling the vacated space, and hemostasis is assessed. FIG. 9 shows hemostasis being confirmed and the guidewire 22 is removed. In FIG. 10, a hemostatic layer has formed at the puncture site, adjacent to the inflated occlusion balloon. FIG. 11 shows the occlusion balloon 82 deflated to assess the stability of the hemostatic layer that has formed at the puncture site 190. In FIG. 12, hemostasis is confirmed and the balloon closure device 10 has been removed, leaving behind a hemostatic plug 198.

The puncture sealing system 10 has particular utility when used in connection with intravascular procedures, such as angiographic dye injection, cardiac catheterization, balloon angioplasty and other types of recanalizing of atherosclerotic arteries, etc. since the puncture sealing system 10 is designed to cause immediate hemostasis of the blood vessel, e.g., arterial, puncture. However, it is to be understood that while the description of the closure device is directed to the closing off of percutaneous incisions or punctures in arteries, it has much more wide-spread applications. Thus, the sealing of a percutaneous opening in an artery shown herein is merely exemplary.

Generally, the puncture sealing system 10 includes an inner member 31 and an outer member 11 and optionally includes or is useable with a guidewire 22. In the embodiment of FIG. 3, the outer member 11 comprises an occlusion catheter 12, and the inner member 31 comprises an anchor/introducer catheter 32 slidably coupled to the occlusion catheter 12. A hub connector 38 or other mechanism may be provided to bias the anchor catheter 32 relative to the occlusion catheter 12. The anchor catheter 32 may also include an inner member expandable member 79, such as an anchor balloon 80 or other expandable member 40, and a vessel locator system 25 coupled to the anchor catheter 32. The occlusion catheter 32 may also include, and an occlusion balloon or other expandable member 82 coupled to the occlusion catheter 12. In this version, the puncture sealing system 10 will be able to use the anchor/introducer catheter 32 to facilitate passage of the puncture sealing system 10 through the puncture tract 190A and puncture 190, to reach the body lumen 194. Otherwise, a peel-away introducer sheath (not shown) may be needed to facilitate such passage.

With reference to FIGS. 1-12, the occlusion catheter 12 may be an elongate tubular body including a proximal end 14, a distal end 16, and a lumen 18 extending therebetween (shown in FIGS. 1-8), thereby defining a longitudinal axis. The occlusion catheter 12 may be flexible, semi-rigid, or rigid, e.g., having a uniform or variable flexibility along its length. The occlusion catheter 12 may be formed from a variety of materials providing a desired rigidity, e.g., plastic, such as polyamide, PEEK, nylon, PET, PEBAX, polyethylene, and/or metal, such as stainless steel or a nickel-titanium alloy, fabricated using known processes, e.g., extrusion, roll forming, machining, and the like. Optionally, a lubricious coating (not shown) may be provided on the exterior of the occlusion catheter 12, e.g., Dow 360 silicone fluid.

The distal end 16 of the occlusion catheter 12 may be attached to the occlusion balloon 82, as explained further below. The distal end 16 may be substantially flexible such that the distal end 16 may curve, bend, or otherwise conform substantially to the contour of the puncture tract 190A into which the distal end 16 is advanced. The occlusion catheter 12 is designed to preferentially remain in the puncture tract 190A and not extend into the puncture 190 and/or body lumen, and as such, it will not enlarge the diameter of the puncture hole. The distal end 16 of the occlusion catheter 12 may have a size sufficient to be inserted into a relatively small puncture tract. For example, the distal end 16 (and possibly the remainder of the occlusion catheter 12) may have an outer diameter between about 0.090-0.120 inch (2.28-3.05 mm). The minimum achievable dimensions of the puncture sealing system 10 and its components may be larger or smaller than mentioned herein. The balloon closure device and its components may be progressively scalable to correspond to the original sheath and puncture size.

The anchor catheter/introducer 32 may be used to facilitate passage of the puncture sealing system 10. Alternatively, a peel-away introducer sheath (not shown) may be provided that is exchanged with the original sheath, to facilitate passage of the puncture sealing system 10, and to facilitate subsequent sheath removal. Exemplary materials for the anchor catheter/introducer 32, and, if needed, the peel-away introducer sheath may include plastics, such as polyamide, PEEK, nylon, PET, PEBAX, and polyethylene, metals, such as stainless steel, and nickel titanium, and/or composite materials.

The anchor catheter/introducer 32, or the peel-away introducer sheath may enhance a rigidity and/or pushability of the puncture sealing system 10, i.e., may be sufficiently rigid to support the puncture sealing system 10, e.g., to prevent the puncture sealing system 10 from buckling or kinking when being advanced through the puncture tract, across a puncture, and into the body lumen, as desired. The anchor catheter/introducer 32 is designed to advance across the puncture 190, and into the body lumen.

In addition, the peel-away introducer sheath may be used to exchange one puncture sealing system 10 for another, e.g., in the event that the anchor balloon 80 ruptures or if a different size anchor balloon is desired. Furthermore, the peel-away introducer sheath may include a side port (not shown) on its proximal end for delivering a fluid.

With continued reference to FIGS. 1-12, the anchor catheter/introducer 32 may be an elongate body including a proximal end 34, and a distal end 36. As can be seen in FIGS. 3-7, the anchor catheter 32 is slidably received within the lumen 18 of the occlusion catheter 12 such that the distal end 36 of the anchor catheter 32 extends beyond the distal end 16 of the occlusion catheter 12. The lumen 18 of the occlusion catheter 12, may have an inner diameter between about 0.068-0.076 inch (1.73-1.93 mm).

When the anchor catheter 32 is disposed within the lumen 18, the distal end 36 of the anchor catheter 32 may extend substantially beyond the distal end 16 of the occlusion catheter 12. The distal end 36 of the anchor catheter 32 may be attached to the anchor balloon 80, as explained further below. The distal end 36 of the anchor catheter 32 may be tapered and may terminate in a substantially flexible and/or atraumatic distal tip, e.g., a "J" tip and the like (not shown).

The anchor catheter 32 may be a hollow wire, hypotube, catheter, and/or the like, formed from a variety of materials, e.g., plastic and/or metal, similar to the occlusion catheter 12. For example, the distal end 36 (and possibly the remainder of the anchor catheter 32) may be polymeric having an outer diameter between about 0.065-0.073 inch (1.65-1.85 mm), and therefore able to pass through the lumen 18 of the occlusion catheter 12. The anchor catheter 32 may include a lumen for receiving a guidewire 22 therethrough, e.g., such that the anchor catheter 32 may be advanced over a guidewire. The guidewire 22 may have an outer diameter between about 0.021-0.025 inch (0.53-0.64 mm). Larger scaled versions of the puncture sealing system 10 may accommodate a standard guidewire with an outer diameter of about 0.035 inch (0.89 mm).

The anchor catheter 32 may be biased to move distally relative to the occlusion catheter 12, so that the anchor catheter 32 may pass through the puncture and enter the body lumen, while the occlusion catheter 12 may remain within the puncture tract.

Turning to FIG. 3, the hub connector 38 may be provided for biasing the anchor catheter 32 relative to the occlusion catheter 12. The hub connector 38 may include cooperating connectors, e.g., hemostatic y connectors (not shown), that may be used for flushing a fluid through the occlusion catheter lumen 18, and for reversibly locking the occlusion catheter 12 to the inner nested anchor catheter 32, as needed. Generally, the hub connector 38 may extend from the proximal end 14 of the occlusion catheter 12. For example, the hub connector 38 may be attached to the proximal end 14 of the occlusion catheter 12 using an adhesive, an interference fit, mating threads, and the like, e.g., to substantially permanently attach the hub connector 38 to the proximal end 14 of the occlusion catheter 12. With the hub connector 38 attached to the occlusion catheter 12, the side port (not shown) may communicate with the occlusion catheter lumen 18. Thus, fluid delivered into the side port may enter the lumen 18.

The side port (not shown) may include a connector, e.g., a luer lock connector, or a nipple (not shown) for connecting tubing or otherwise connecting a source of fluid (not shown) to the side port. For example, a syringe (not shown) filled with fluid, e.g., saline, and the like, may be connected to the side port for manually delivering the fluid into the lumen 18. Alternatively, a pump or other device (not shown) may be provided for delivering fluid at a desired pressure and/or flow rate.

The hub connector 38 may include a hemostatic connector (not shown) with an adjustable central aperture (not shown). The distal end 36 of the anchor catheter 32 may be inserted into the aperture, allowing the anchor catheter 32 to pass through the occlusion catheter lumen 18, across the puncture, and into the body lumen. The anchor catheter 32 may be fixed in an axial position relative to the occlusion catheter 12, by tightening the central aperture of the hemostatic connector of the hub connector 38, for example, using a compression spring, a hemostatic valve, or other mechanism, as is known in the art. The proximal ends of the occlusion catheter 12 and anchor catheter 32, may each include annular bands or other markers (not shown) thereon that may become aligned when the distal ends of the catheters are offset as desired, as discussed below.

The anchor balloon 80 and the occlusion balloon 82 may each be inflated by using a viscous fluid (i.e., a fluid more viscous than air). This should avoid the introduction of any significant amount of air into any body lumen where air does not belong. Preferentially, fluid may be injected into the balloon using a predetermined volume that will achieve a desired balloon diameter based on the balloon's compliance characteristics. If a predetermined pressure is needed for proper balloon inflation, then some type of visual indication or gauge may be provided to indicate that the predetermined pressure has been reached. The predetermined pressure may correspond to a desired maximum pressure for a balloon, e.g., to ensure that the balloon is expanded to a desired diameter and/or to prevent risk of the balloon rupturing.

Turning to FIGS. 3-11, the anchor balloon 80 and the occlusion balloon 82 may each be reversibly expandable from a collapsed state to an expanded state when an inflation medium (not shown) is introduced into the interior of each balloon. In an alternative embodiment, other expandable members, e.g., a mechanically expandable or self-expanding member (not shown) may be provided instead of a balloon.

The anchor balloon 80 and the occlusion balloon 82 may each be formed from a flexible, substantially inelastic material, e.g., a nonelastomeric material, such as PET, nylon, PEBAX, and the like, that may provide a substantially noncompliant balloon that may expand to a predetermined size once a minimum pressure is introduced into the interior. In this embodiment, the size of the balloons 80 and 82 in the expanded state may be fixed. Alternatively, the balloons 80 and 82 may each be formed from an elastic material, such as POC, polyethylene, polyurethane, silicone, and the like, such that the size of the anchor balloon 80 and the occlusion balloon 82 in the expanded state is dependent upon the volume of fluid delivered within the interior, as is known in the art.

In one embodiment, as seen in FIG. 6, the anchor balloon 80 includes a proximal end 84, a distal end 86, and an expandable intermediate section defining the interior 71 of the anchor balloon 80. The proximal and distal ends 84 and 86, respectively, of the anchor balloon 80 may be attached to the distal end 36 of the anchor catheter 32, but, preferably, proximal to its tapered tip. The interior 71 of the anchor balloon 80 may communicate with the balloon inflation lumen 35 of the anchor catheter 32. Similarly, the occlusion balloon 82 includes a proximal end 83, a distal end 85, and an expandable intermediate section defining the interior 72 of the occlusion balloon 82. The proximal end 83 of the occlusion balloon 82 may be attached to the distal end 16 of the occlusion catheter 12, and the distal end 85 of the occlusion balloon 82 may be attached to or may extend beyond the distal end 16 of the occlusion catheter 12. The interior 72 of the occlusion balloon 82 may communicate with the balloon inflation lumen 15 of the occlusion catheter 12.

As can be seen, in FIG. 6, the proximal end 84 and distal end 86 of the anchor balloon 80 may overlie and be attached to the distal end 36 of the anchor catheter 32, e.g., using an adhesive, sonic welding, crimping, a compressive sleeve, an interference fit, and/or the like. Similarly, the proximal end 83 and the distal end 85 of the occlusion balloon 82 may overlie and be attached to the distal end 16 of the occlusion catheter 12, e.g., using an adhesive, sonic welding, crimping, a compressive sleeve, an interference fit, and/or the like.

The distal end 86 of the anchor balloon 80 may be attached proximal to the tapered portion of the anchor catheter 32 and not extend beyond the distal end 36 of the anchor catheter 32, e.g., to allow for the least diameter profile for the distal tip of the anchor catheter 32. The anchor balloon 80 may have a length of at least about five millimeters (5 mm). The distal end 85 of the occlusion balloon 82 may extend beyond and wrap around the distal end 16 of the occlusion catheter 12 and may extend into the occlusion catheter lumen 18. This design may allow the occlusion balloon to inflate and atraumatically occlude both the puncture and the puncture tract, over time facilitating hemostasis within a puncture in a wall of a body lumen. The occlusion balloon 82 may have a length of at least about twenty millimeters (20 mm) on the outer surface of the occlusion catheter 12 and possibly a length of at least about ten millimeters (10 mm) on the inner luminal surface of the occlusion catheter 12. This length is based on the punctured blood vessel and the length of its associated puncture tract requiring occlusion, e.g. the femoral artery versus the radial artery which has a very short puncture tract.

In the collapsed state, shown in FIGS. 3 and 4, the anchor balloon 80 and/or occlusion balloon 82 may conform substantially to the diameter of the anchor catheter 32 and occlusion catheter 12, respectively. The anchor balloon 80 is expanded to the expanded state, shown in FIGS. 5 and 6, by introducing an inflation medium (not shown) into the balloon inflation lumen 35 of the anchor balloon 80, and consequently into the interior 71 of the anchor balloon 80. The occlusion balloon 82 is expanded to the expanded state, shown in FIGS. 6-10, by introducing an inflation medium (not shown) into the balloon inflation lumen 15 of the occlusion balloon 82, and consequently into the interior 72 of the occlusion balloon 82. The balloon inflation lumens may each include one or more seals (not shown), separate lengths of tubing, a hemostatic adapter, stopcock, and the like, attached, to its proximal end, e.g., to prevent substantial proximal flow of fluid through the lumen and to maintain balloon inflation pressure, as is known in the art.

Optionally, not shown, the puncture sealing system 10 may include other components, e.g., to provide a kit for performing a procedure on a patient. For example, an introducer sheath, such as a valved hemostatic peel-away introducer sheath, may be provided that includes a proximal end, a distal end, and a lumen extending therebetween. The introducer sheath may include a dilator with a tapered distal tip that may be inserted into the lumen of the introducer sheath, e.g., for facilitating advancing the introducer sheath through a puncture, as is known to those skilled in the art. In addition, the introducer sheath may include a side port on the proximal end communicating with the lumen and/or may include one or more seals (not shown), e.g., to prevent substantial proximal flow of fluid through the lumen, as is known in the art. The side port may include one or more components, e.g., separate lengths of tubing, stopcocks and the like (not shown), as will be appreciated by those skilled in the art. In addition, the kit may include a syringe, not shown, or other device for delivering fluid into the side port of the introducer sheath, as well as for delivering inflation medium into the balloon inflation lumens, as explained above. A syringe may be connected to the side port of the introducer sheath for injecting fluid into the introducer sheath lumen, and similarly into ports located on the proximal ends of the balloon inflation lumens.

Optionally, the kit may also include a stylet or obturator (not shown) that may be inserted into the lumen of the introducer sheath, e.g., to facilitate percutaneously inserting the introducer sheath through tissue, as is known to those skilled in the art. In addition, or alternatively, one or more guidewires (not shown) may also be provided.

Turning to FIGS. 1-21, a method for sealing a passage through tissue is shown. The passage may be a percutaneous puncture extending from a patient's skin to a blood vessel or other body lumen. For example, the vessel may be a peripheral artery or vein, e.g., a femoral artery, a femoral vein, a carotid artery, and the like.

Before further describing the use of the puncture sealing system 10 to seal a puncture, a brief description of a typical, conventional, intravascular surgical procedure, e.g., catheter instrumentation of an artery, utilizing a percutaneous opening will be given to best appreciate the features of the invention. In such a procedure a cannula of an instrument, such as an angiographic needle (not shown), is inserted percutaneously through the skin into the artery, such as the femoral artery, at the situs for the closure device's insertion. The needle cannula is held in place and the flexible end of a mini-guidewire (not shown) is then passed through the cannula into the artery to the desired depth (i.e., longitudinal position therealong). Once the mini-guidewire is in place the needle cannula is removed, leaving the guidewire in place. An introducer sheath (not shown) and an arterial dilator (not shown) are then passed over the guidewire, through the puncture or incision and into the artery. The guidewire and then the dilator are removed leaving the introducer sheath in place.

One or more instruments (not shown) may be advanced through the introducer sheath and into the vessel, e.g., to perform a diagnostic and/or therapeutic procedure within the patient's body, e.g., threaded down the artery to the desired intravascular location, e.g., the situs of the atherosclerotic occlusion. The one or more instruments may include catheters, e.g., balloon catheters, stent delivery catheters, imaging catheters, and the like, guidewires, and/or other devices. Upon completing the intravascular procedure(s), any instruments may be removed. Thereafter, the sheath is removed and a physician or other trained person applies manual, digital pressure to the percutaneous puncture until hemostasis has occurred. In particular, the current standard of care for puncture hemostasis is to apply digital or mechanical pressure on the puncture site for twenty minutes to an hour, depending on the puncture size and the degree of hemolytic therapy. Obviously, this results in wasted time for the physicians and other catheter lab personnel, and causes inconvenience and discomfort for the patient. In addition, serious complications arise from persistent bleeding and hematoma formation in approximately five percent of the patients. A much better option is to employ a system to seal the arterial puncture site 190 and plug the puncture tract 190A, such as that shown in FIGS. 1-21 and described above. Moreover, as will be appreciated from the description to follow, the puncture sealing system 10 is designed to reduce post-procedure puncture complications, cause minimal inflammatory reaction, and leave nothing behind in the vessel or puncture tract.

Turning to FIGS. 3 and 4, with the anchor balloon 80 and the occlusion balloon 82 in the collapsed state, and using the anchor catheter 32 as an introducer, the puncture sealing system 10 may be inserted through the puncture tract lumen 190A, over the device exchange guidewire 22, until the anchor catheter's distal end has passed through the puncture 190 and is disposed within the vessel 194. This may be indicated by the vessel locating system 25. With the vessel locating system 25 blood enters one or more intraluminal ports referred to as vessel locator distal holes 28, passes through a marker lumen 27, and exits through one or more vessel locator proximal holes 26. The one or more vessel locator distal holes 28, marker lumen 27, and one or more vessel locator proximal holes 26 may all be an integral part of the anchor catheter 32 or may be separable therefrom. The marker lumen 27 allows a pathway for back-bleeding (obtaining mark) from the body lumen, e.g., a femoral artery, to ensure proper device positioning.

Optionally, the puncture sealing system 10 may include one or more markers, e.g., radiopaque markers (not shown), to facilitate monitoring insertion of the system 10 using external imaging, e.g., fluoroscopy, ultrasound, magnetic resonance imaging ("MRI"), and the like.

Alternatively or in addition, one or more visual markers (not shown) may be provided, e.g., on the proximal end 34 of the anchor catheter 32, and on the proximal end 14 of the occlusion catheter 12, respectively. The markers may include one or more colored bands at predetermined locations along a length of the anchor catheter 32 relative to the anchor balloon 80. For example, a distance between a band on the proximal end 34 of the anchor catheter 32 may correspond to a length of the anchor catheter 32, thereby providing a visual indication when the anchor catheter 32 has been advanced sufficiently to expose the anchor balloon 80 beyond the distal end 16 of the occlusion catheter. Similarly, the markers may include one or more colored bands at predetermined locations along a length of the occlusion catheter 12 relative to the distal end 16 of the occlusion catheter 12, with the distance between bands corresponding to the length of insertion of the occlusion catheter 12 into the puncture tract 190A. Together, these markers may provide a visual indication when the puncture sealing system 10 has been advanced sufficiently through the puncture and into the vessel lumen.

As shown in FIGS. 4 and 5, once the anchor balloon 80 is disposed within the vessel lumen and blood is exiting the vessel locator proximal hole 26, the anchor balloon 80 may be expanded to the expanded state, e.g., by introducing fluid into the anchor balloon inflation lumen 35 through the anchor catheter 32 and into the anchor balloon 80. A prescribed amount of fluid may be introduced so that the anchor balloon 80 may be expanded to a desired size. An additional mechanism may be provided to inform the user that a desired pressure has been reached within the anchor balloon. In addition, one or more mechanisms may be provided to prevent deflation of the anchor balloon including a stopcock, and possibly a hemostatic valve connected to the balloon inflation lumen. The hemostatic valve may have a quick connect adapter requiring a syringe to be attached and locked into the adapter before inflation or deflation may occur.

The anchor catheter 32 may be removed, if desired. For example, if the anchor balloon 80 accidentally ruptures, the anchor catheter 32 may be removed and replaced with another anchor catheter having an intact balloon (not shown). In addition or alternatively, if it is discovered that the anchor balloon 80 is the wrong size for the given anatomy (e.g., is too small for the puncture or too large for the vessel), the anchor catheter 32 may be replaced with one having a larger or smaller balloon. This may be avoided by the anchor balloon 80 having a range of possible sizes based on its degree of inflation.

As shown in FIG. 5, the anchor catheter 32 may be partially withdrawn from the arterial lumen with the anchor balloon 80 in the expanded state, i.e., until the anchor balloon 80 engages (catches) on the artery wall contiguous with the puncture. Preferably, the anchor balloon 80 substantially seals the puncture 190, i.e., substantially isolating the puncture 190 from the arterial lumen 194. Thus, the puncture sealing system 10 may provide temporary hemostasis, e.g., preventing blood from passing through the puncture 190. Thus, even without the additional steps that follow, the puncture sealing system 10 may be used to provide hemostasis in emergency situations in order to minimize loss of blood until a puncture victim may be treated.

The anchor balloon 80 in the expanded state, as described above, may be particularly suited for providing hemostasis, while still allowing blood flow to continue along the arterial lumen 194. For example, as shown in FIG. 5, the diameter of the anchor balloon 80 may be substantially greater than its length in the expanded state. Thus, when the anchor balloon 80 is pulled into engagement with the arterial wall 196 of the arterial lumen 194, at least a portion of the arterial lumen 194 may remain unobstructed, as shown.

As shown in FIG. 6, with an individual applying a proximal force to the anchor catheter 32 in order to maintain the anchor balloon 80 substantially against the puncture 190, the occlusion catheter 12 may be advanced to the distal end of the puncture tract 190A and the anchor catheter 32 and occlusion catheter 12 may be locked together at the hub connector 38. While reapplying a proximal force to the anchor catheter 32 in order to maintain the anchor balloon 80 substantially against the puncture 190, the occlusion balloon 82 may be inflated against the exterior of the artery contiguous with the puncture 190 to occlude the puncture and the puncture tract 190A. The puncture sealing system 10 is now essentially locked in place in the puncture tract. If needed, a tensioner (not shown) may be provided that may apply a proximal force to the anchor catheter 32 to maintain the anchor balloon 80 substantially against the puncture 190. The tension imposed by the tensioner may apply a desired tensile force to the anchor balloon 80 to maintain hemostasis while preventing the anchor balloon 80 from being pulled into the puncture 190 and/or preventing the arterial wall 196 of the arterial lumen 194 from excessive tenting.

The occlusion balloon 82 may optionally be coated with a hemostasis-promoting material (not shown), e.g. chitosan, which may promote hemostasis within the puncture tract 190A. Because of the hemostasis provided by the anchor balloon 80, the hemostasis-promoting material on the occlusion balloon may be delivered to the puncture tract without substantial concern that the hemostasis-promoting material may leak into the arterial lumen 194.

As shown in FIGS. 7 AND 8, once the occlusion balloon 82 is fully inflated, the anchor balloon 80 may then be deflated to the collapsed state, and hemostasis may be assessed. Once hemostasis is confirmed, the anchor catheter 32 may then be withdrawn from the puncture 190, into the puncture tract 190A, and removed from the body. Similarly, as shown in FIG. 9, the device exchange guidewire 22 may be withdrawn from the puncture 190, into the puncture tract 190A, and removed from the body.

A syringe or other device (not shown) may be used to evacuate fluid via the side port of the balloon inflation lumen 35 to collapse the anchor balloon 80. Once fluid is removed, and the anchor balloon 80 is in the collapsed state, the anchor balloon 80 may be withdrawn through the puncture 190 and puncture tract 190A without substantially disturbing the inflated occlusion balloon 82. To facilitate removing the anchor balloon 80, a lubricious coating (not shown) may be provided on the exterior of the anchor balloon 80, e.g., Dow 360 silicone fluid. Such a coating may prevent the anchor balloon 80 from sticking to or otherwise pulling on the occlusion balloon 82 as the anchor balloon 80 is withdrawn.

The occlusion balloon may remain inflated in the tissue tract for a time duration based on patient-related factors including the size of the puncture and the patient's level of anticoagulation. This time duration may range from minutes to hours. With very large punctures, maintaining puncture tract occlusion overnight may also be a suitable option, while still allowing unobstructed blood flow to continue along the arterial lumen 194. It may be possible that, with the occlusion balloon inflated, a patient may ambulate without compromising the hemostatic process.

As shown in FIGS. 10 and 11, after sufficient time has elapsed, the occlusion balloon 82 may be deflated and hemostasis assessed, possibly both at rest and with ambulation. As shown in FIG. 12, once hemostasis is confirmed, the puncture sealing system 10 may be completely removed from the body, leaving nothing behind but the body's own hemostatic plug 198.

Figure 14:
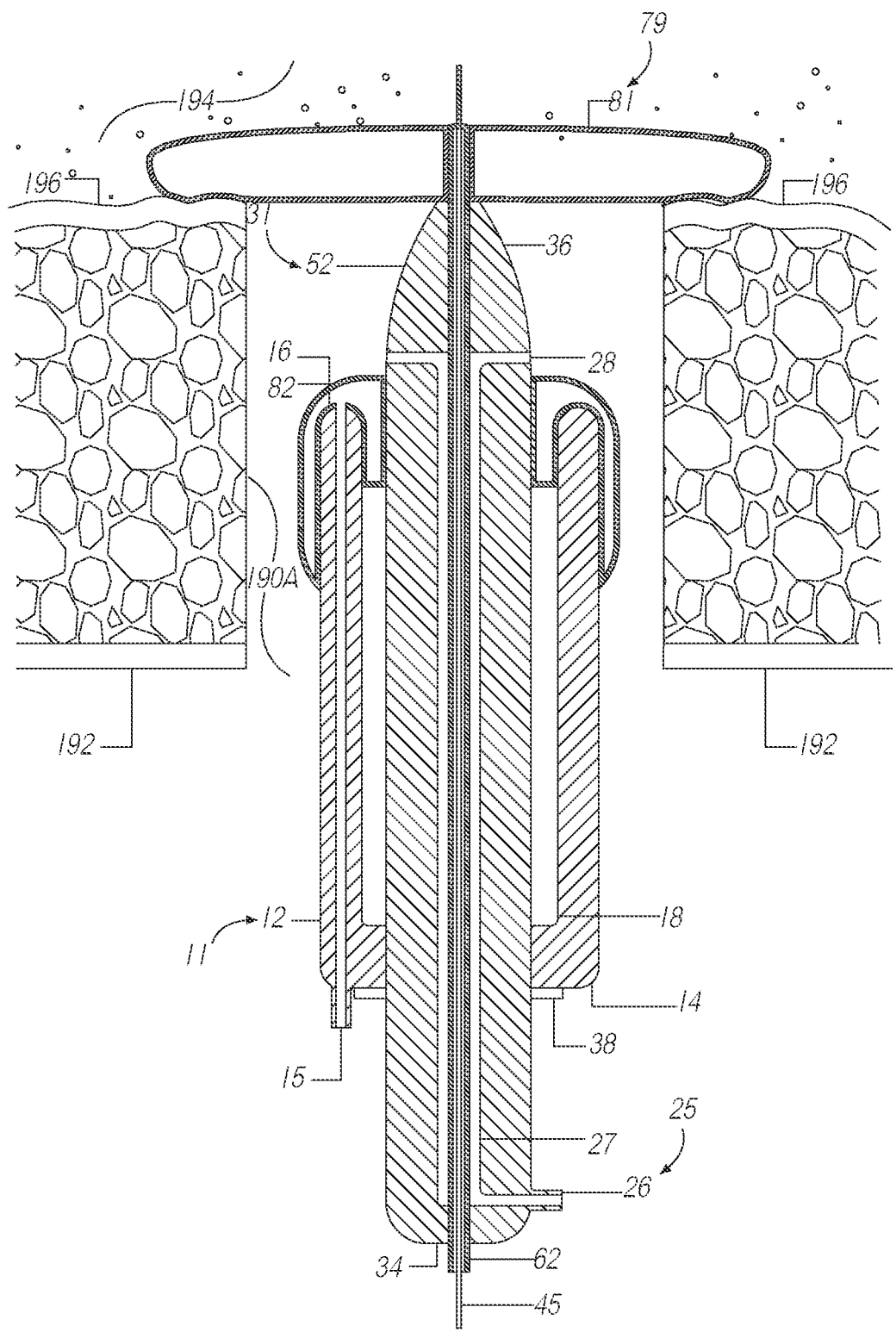
FIG. 14 is a schematic sectional representation of the embodiment of FIG. 13 in use showing an alternative anchor balloon.
Figure 15:
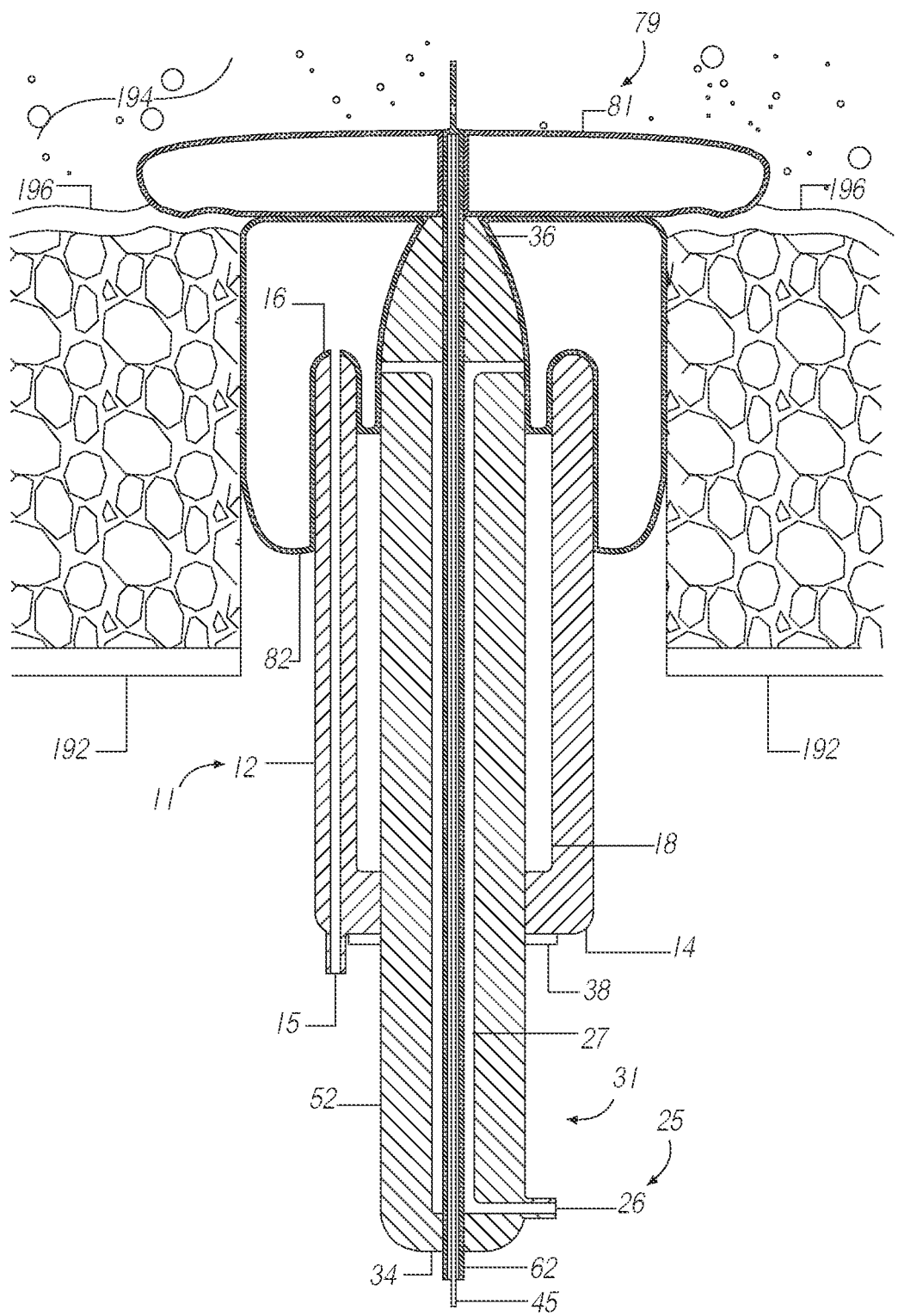
FIG. 15 is a schematic sectional representation of the embodiment of FIG. 13 in use showing an occlusion catheter is advanced to the distal end of a puncture tract.
Figure 16:
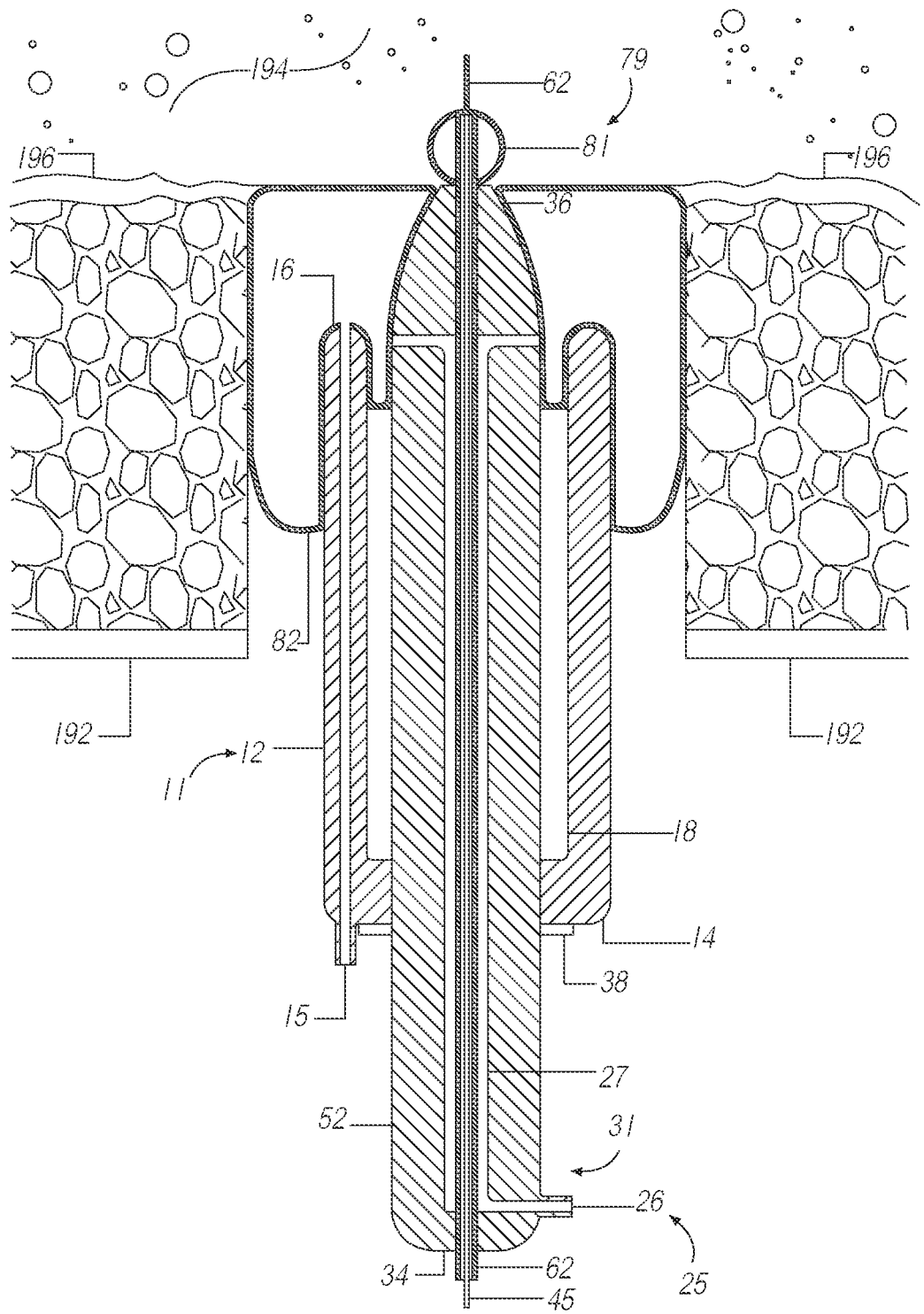
FIG. 16 is a schematic sectional representation of the embodiment of FIG. 13 in use showing an alternative anchor balloon deflated and an inflated occlusion balloon.
Figure 17:
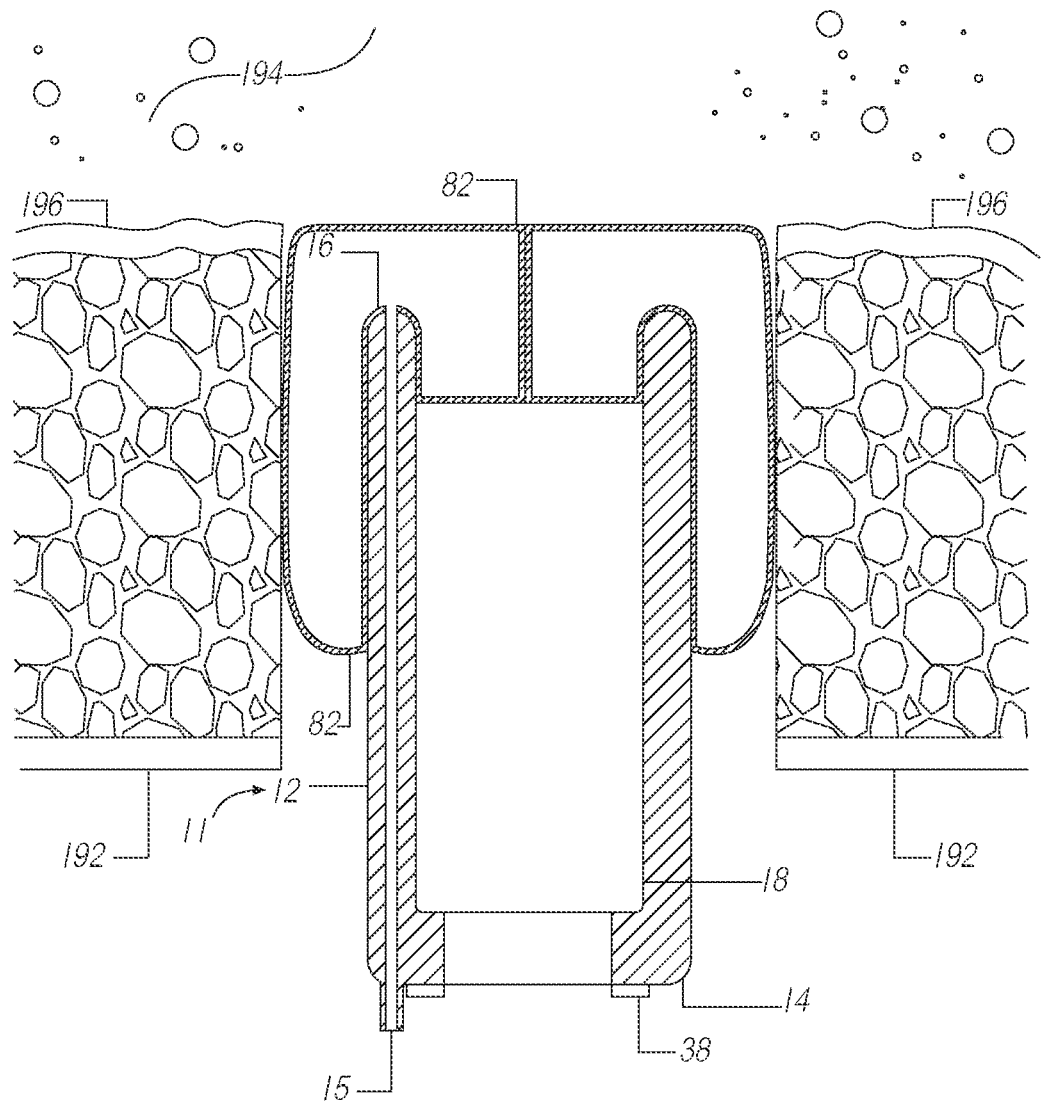
FIG. 17 is a schematic sectional representation of the embodiment of FIG. 13 in use showing a dilator/introducer and alternative anchor balloon are removed and an occlusion balloon filling the vacated space.
Figure 18:
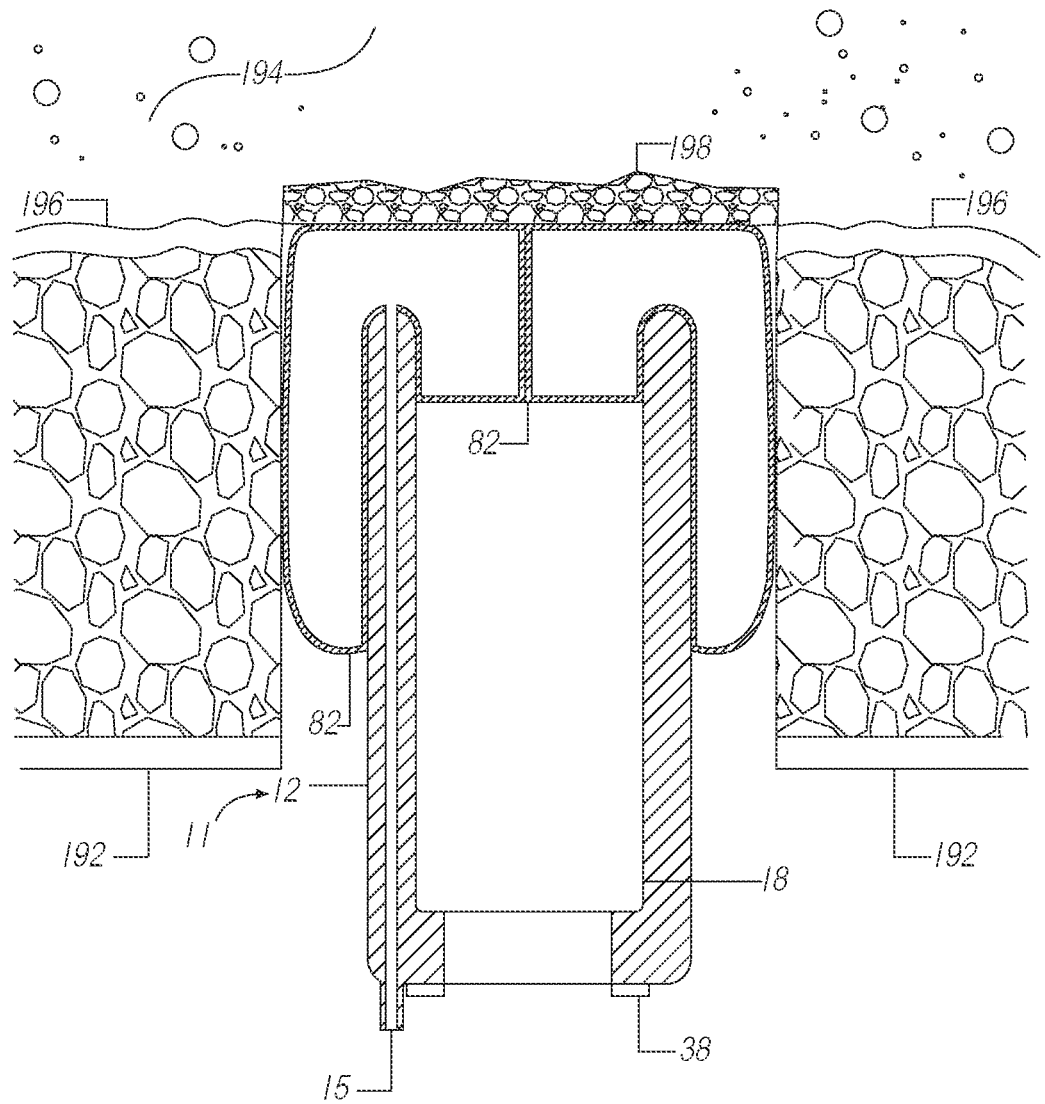
FIG. 18 is a schematic sectional representation of the embodiment of FIG. 13 in use showing a hemostatic layer formed at a puncture site.
Figure 19:
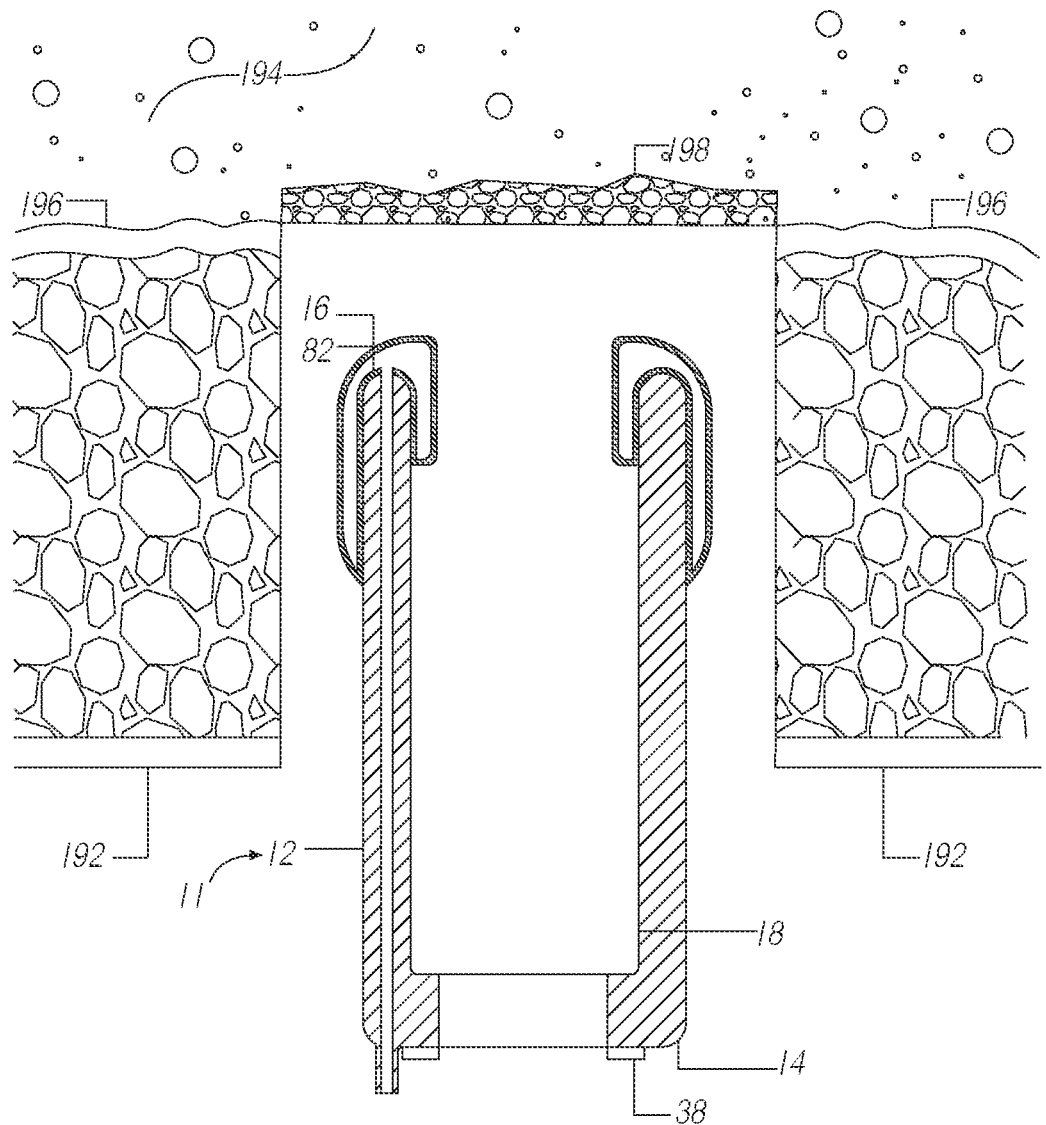
FIG. 19 is a schematic sectional representation of the embodiment of FIG. 13 in use showing an occlusion balloon deflated to assess the stability of a hemostatic layer that has formed at a puncture site.
Figure 20:
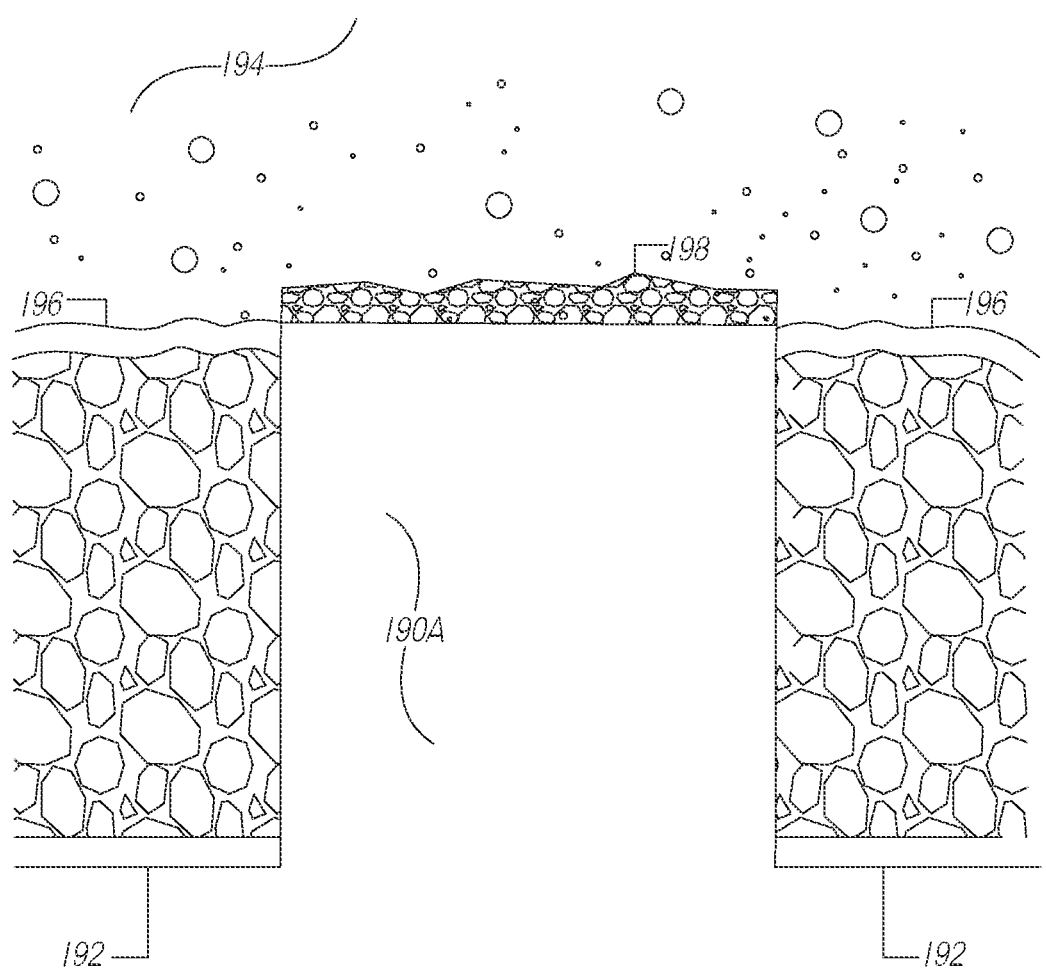
FIG. 20 is a schematic sectional representation of hemostasis is confirmed after a balloon closure device has been removed, leaving behind a hemostatic plug.
Figure 21A:
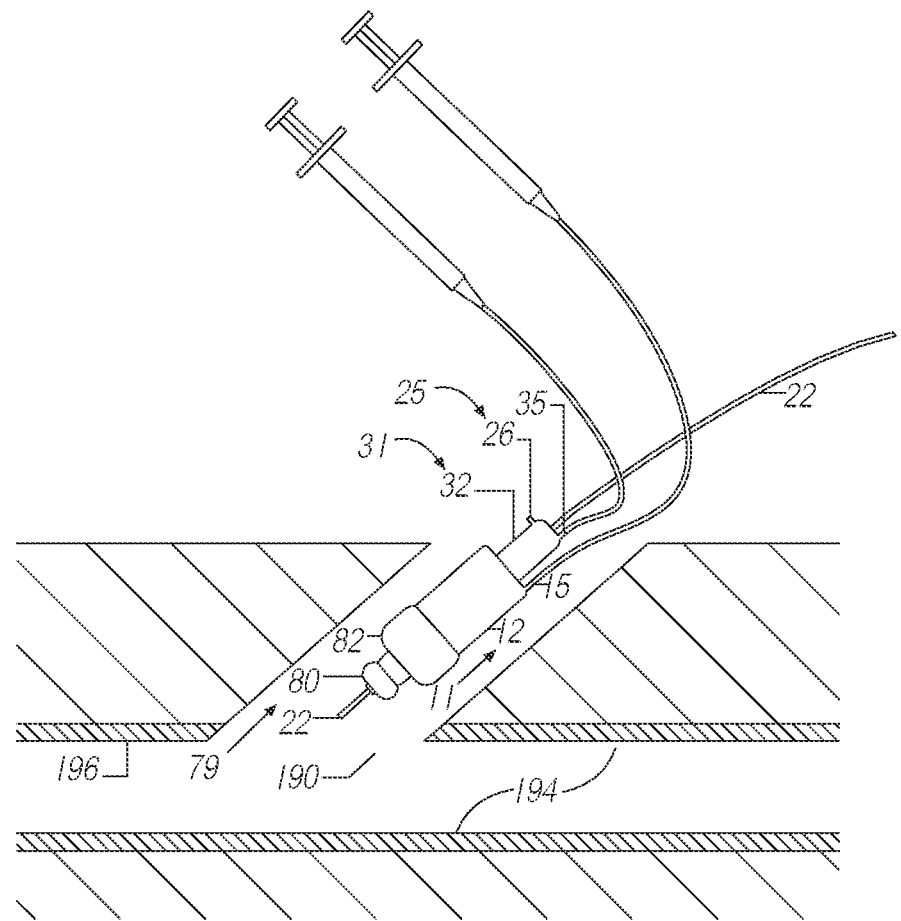
FIG. 21A is a partially sectional side view of a percutaneous puncture communicating with a blood vessel showing a step of a method for sealing the puncture, in accordance with the present invention.
Figure 21B:
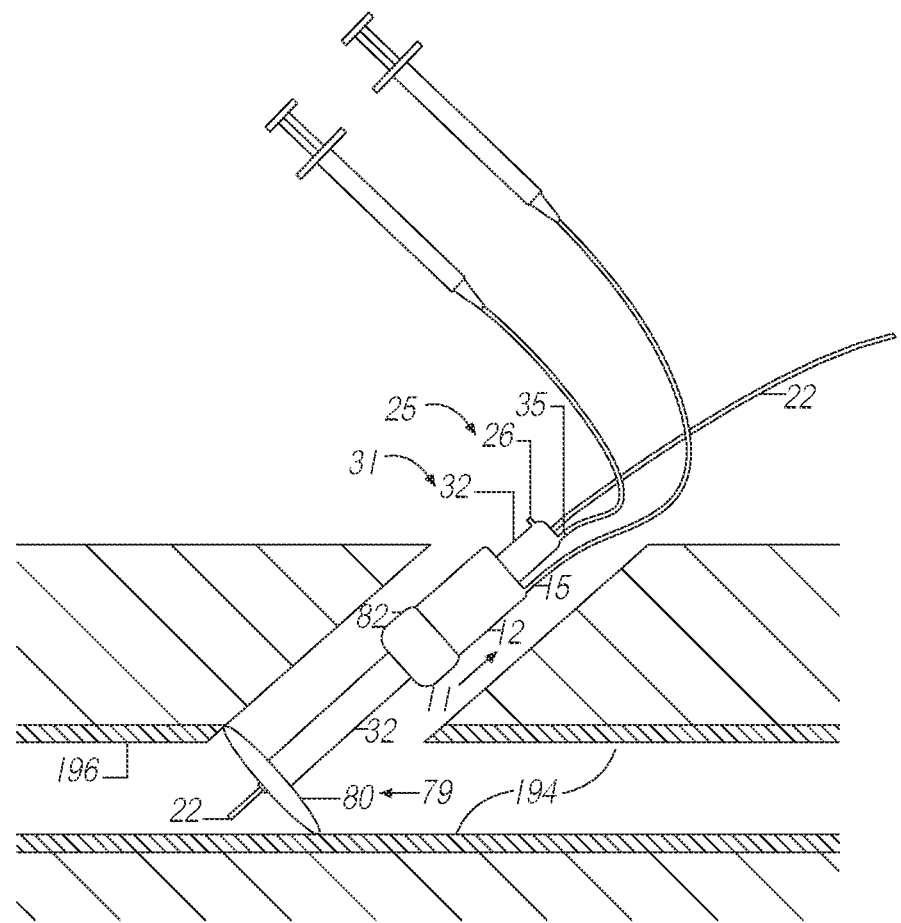
FIG. 21B is a partially sectional side view of a step subsequent to the step shown in FIG. 21A.
Figure 21C:
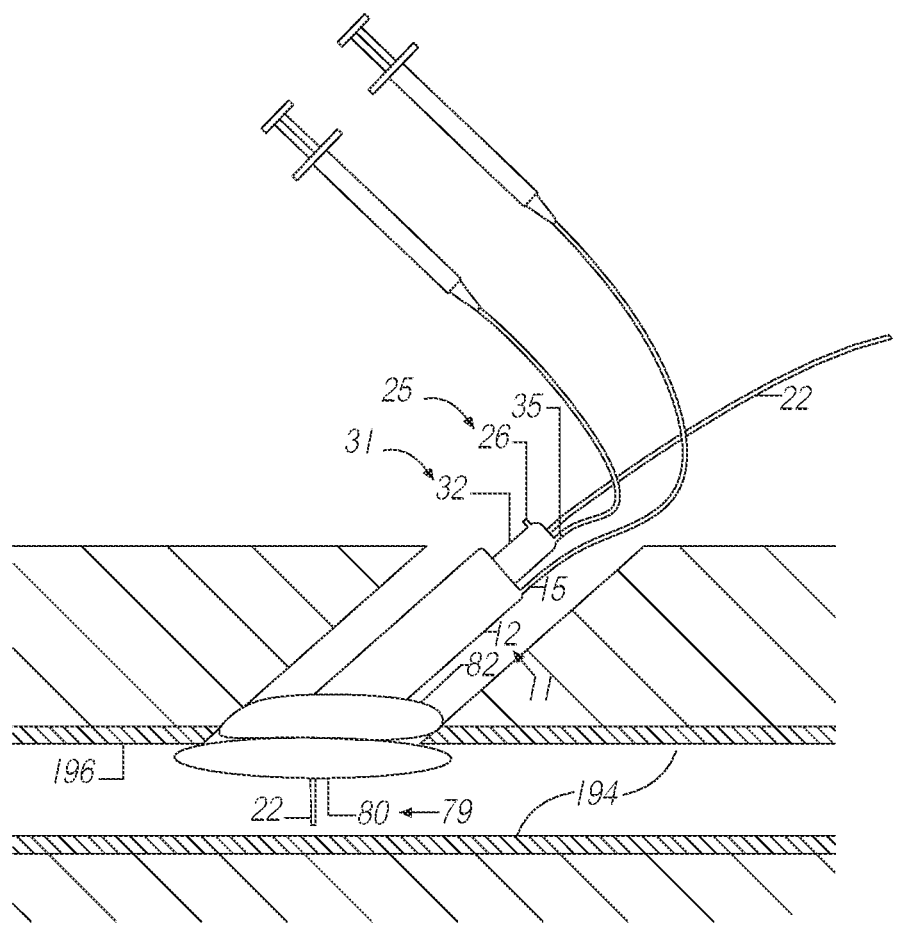
FIG. 21C is a partially sectional side view of a step subsequent to the step shown in FIG. 21B.
Figure 21D:
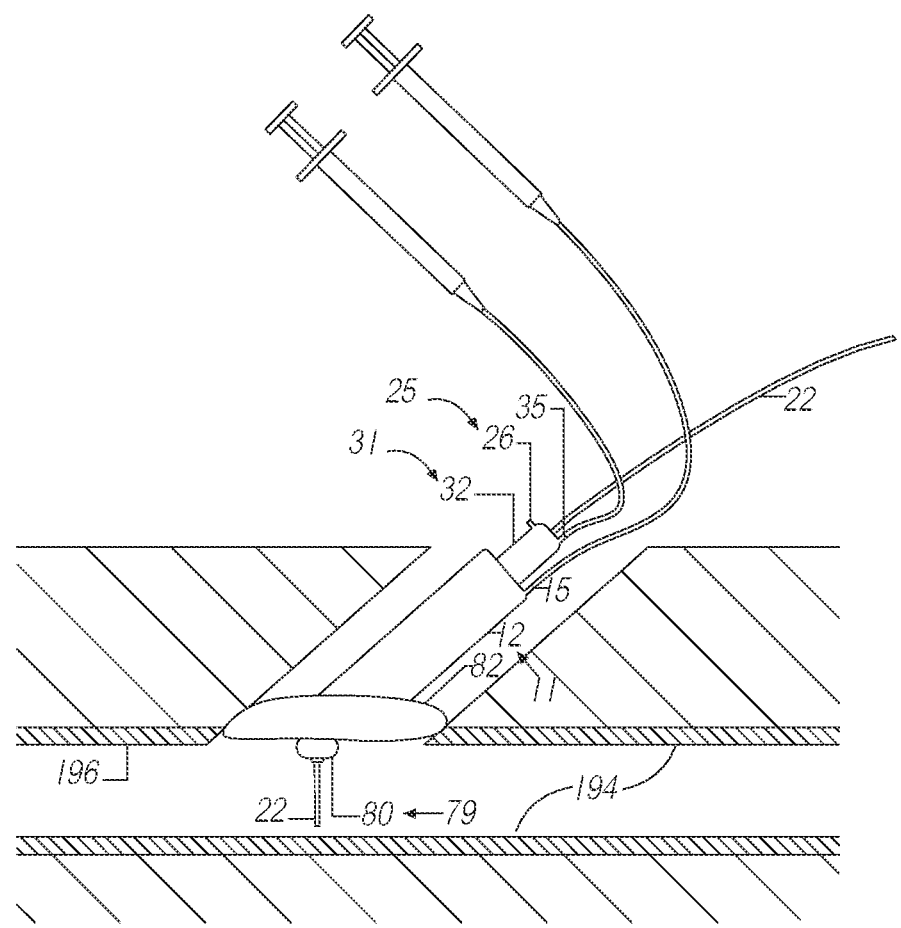
FIG. 21D is a partially sectional side view of a step subsequent to the step shown in FIG. 21C.
Figure 21E:
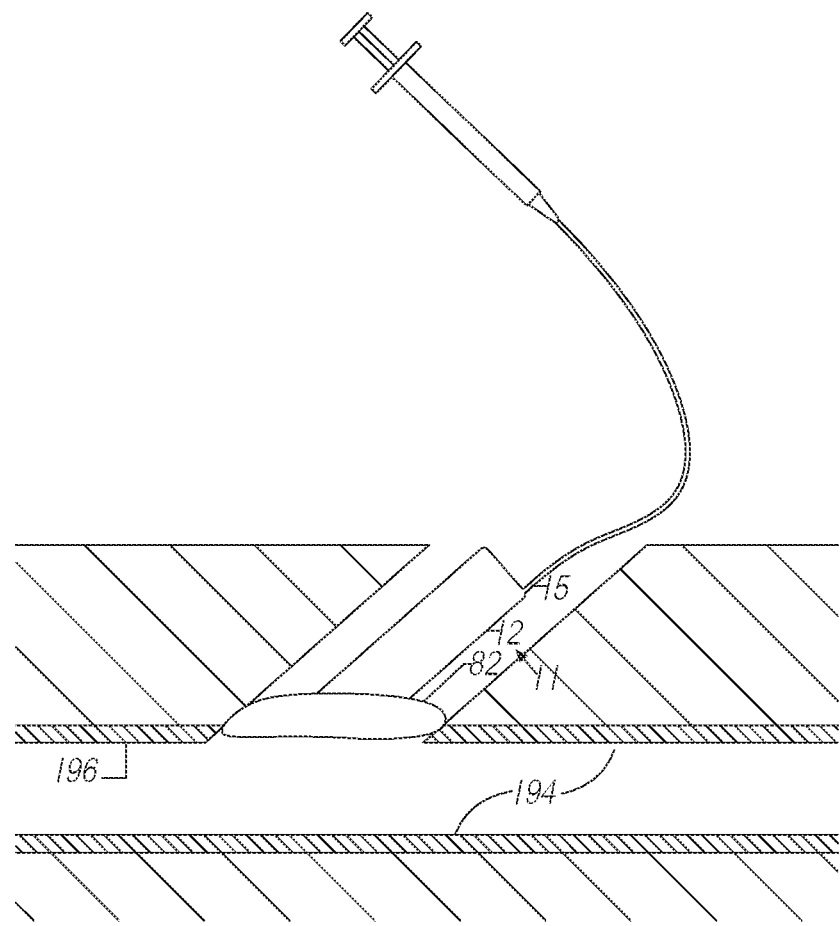
FIG. 21E is a partially sectional side view of a step subsequent to the step shown in FIG. 21D.
Figure 21F:
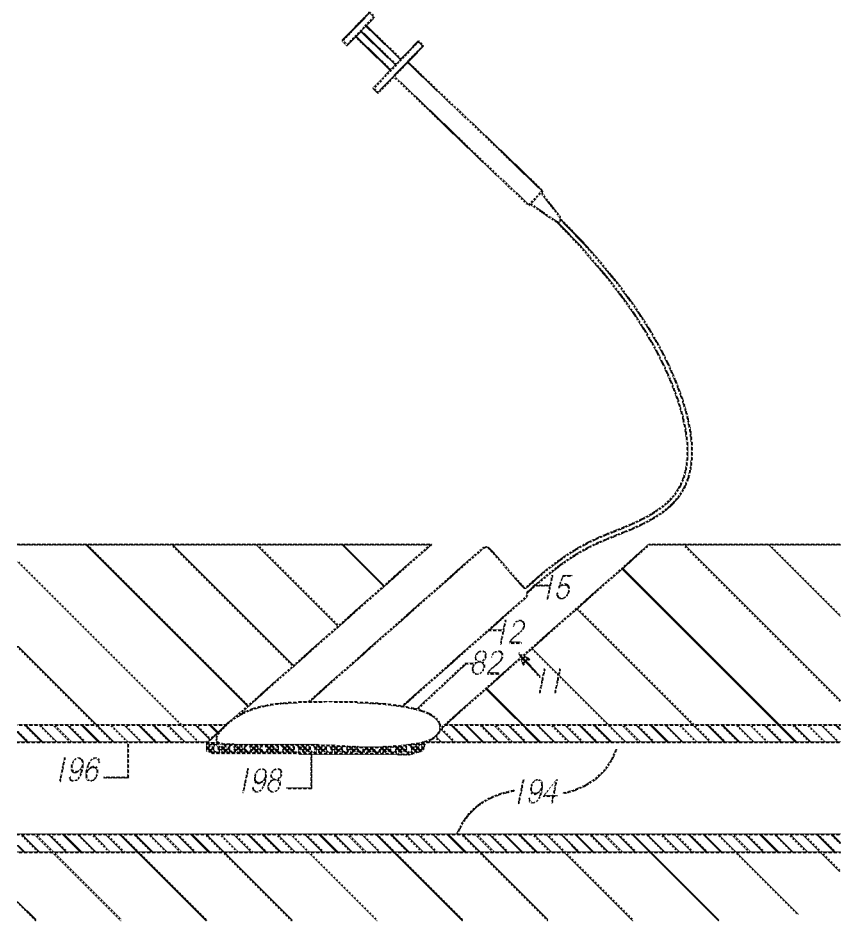
FIG. 21F is a partially sectional side view of a step subsequent to the step shown in FIG. 21E.
Figure 21G:
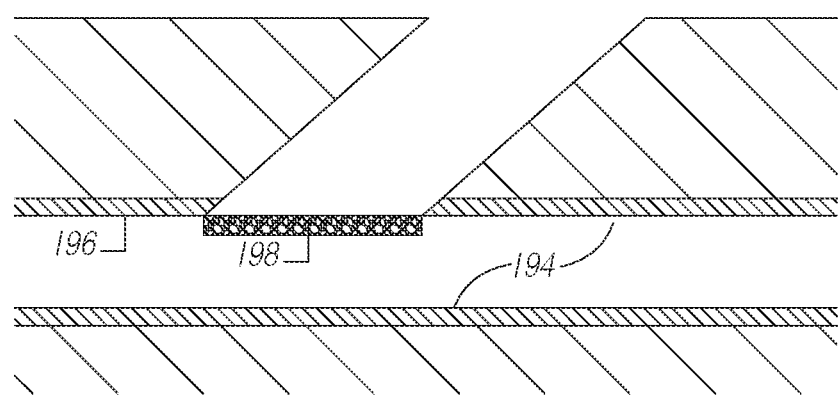
FIG. 21G is a partially sectional side view of a step subsequent to the step shown in FIG. 21F.

FIGS. 13-20 demonstrate another embodiment of a puncture sealing system 10 according to the invention. The embodiment of FIGS. 13-20 may result in a smaller profile balloon closure device. In this embodiment, an inner catheter system includes a first catheter, the inner member 31, which comprises a low profile dilator/introducer 52 instead of the anchor catheter. Like the anchor catheter 32 in the embodiment of FIGS. 3-12, the dilator/introducer 52 may have a vessel locator system 25 to indicate entry into the blood vessel lumen. The dilator/introducer 52 in this version may lack an anchor balloon and guidewire. The inner catheter system further includes a second catheter, a simple balloon catheter 62, as is known in the art, that may be advanced through the guide wire lumen, enter the blood vessel and function similarly to the anchor balloon 80. As shown in FIG. 14, the inner catheter system expandable member 79 comprises a balloon catheter balloon 81 that may be inflated through lumen 45 and pulled back along with the dilator/introducer 52, to maintain the balloon catheter balloon 81 substantially against the puncture 190. The subsequent steps demonstrated in FIGS. 15-20 are substantially similar to those previously demonstrated in FIGS. 6-12, and described previously.

As may be appreciated by the description above, deployment of the balloon closure device is easy, quick, reliable, and should avoid significant discomfort to the patient. Hemostasis occurs almost instantaneously, e.g., in 15 seconds or less, when the closure device is deployed properly.

Should there be any residual bleeding from the puncture tract or arterial lumen, external pressure may be applied, e.g., by pressing manually against the skin 192 overlying the arterial lumen 194. External pressure may be maintained for sufficient time to allow substantial sealing of any residual bleeding remaining upon removing the puncture sealing system 10.

As should be appreciated from the foregoing, the closure device, and its method of use, as shown in FIGS. 21A through 21G, enables the ready, effective and efficient sealing of a percutaneous puncture in an artery (or vein). Thus, it is expected that the puncture sealing system 10 will be a significant advancement in the fields of cardiology and radiology. The device may allow continuance of anticoagulation post-procedure, more aggressive use of thrombolytic agents and safer use of large bore catheters. It should also reduce discomfort and complication rates for patients. It may allow early or even immediate ambulation with the device "locked" in place. It may allow many in-patient procedures to be performed safely on an out-patient basis, decrease the time and cost of interventional procedures, and reduce exposure of hospital personnel to human blood.

FIGS. 22-28 show another embodiment of a puncture sealing system 10 according to the invention. The embodiment of FIGS. 22-28 shares many features and similarities with the embodiment of FIGS. 3-12. For example, the embodiment of FIGS. 22-28 has an inner member 31, such as an anchor catheter 32 that is slidably received within an outer member 11, such as an occlusion catheter 12. The anchor catheter 32 has an expandable member 79 in the form of an anchor balloon 80, and the occlusion catheter 12 has an occlusion balloon 82 near the occlusion catheter distal end 16. In the embodiment of FIGS. 22-28, the occlusion balloon proximal end 83 extends to the distal end 16 at a position proximal to the distal tip 17 of the distal end 16 in similar manner as the embodiment of FIGS. 3-12. The distance of the attachment of the proximal end 83 to the distal tip 17 corresponds generally to the amount of puncture tract 190A that is to be occluded. For example, the distance from the attachment of the proximal end 83 to the distal tip can range from about 20 mm to about 40 mm and in one particular version is about 30 mm. In the embodiment of FIGS. 22-28, the occlusion balloon distal end 85 is attached to the occlusion catheter 12 at or just proximal to the distal tip 17. Unlike the embodiment of FIGS. 3-12 where the occlusion balloon 82 wraps around the distal end 16 of the occlusion catheter 12 so that the inflated occlusion balloon 82 can cover substantially the entire puncture 190, in the embodiment of FIGS. 22-28, the occlusion balloon 82 does not extend beyond the distal end 16 of the occlusion catheter 12 and/or does not wrap around the distal end 16 of the occlusion catheter 12. Accordingly, in this version, the inflated occlusion balloon does not cover the entire puncture 190 and covers only a portion of the puncture 190 or does not cover any of the puncture 190.

Figure 22:
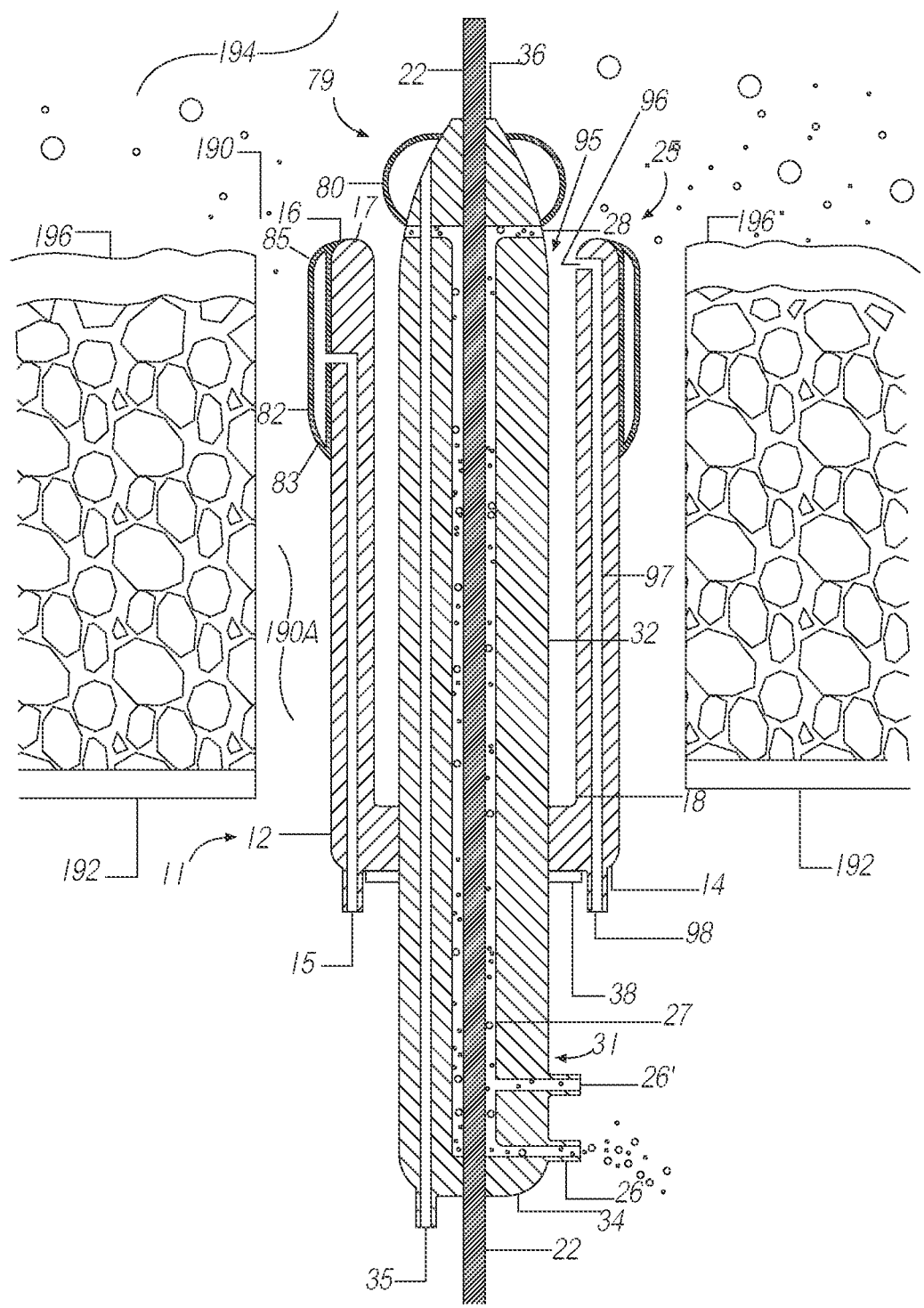
FIG. 22 is a schematic sectional representation of another embodiment of a puncture sealing system in accordance with the present invention.
Figure 23:
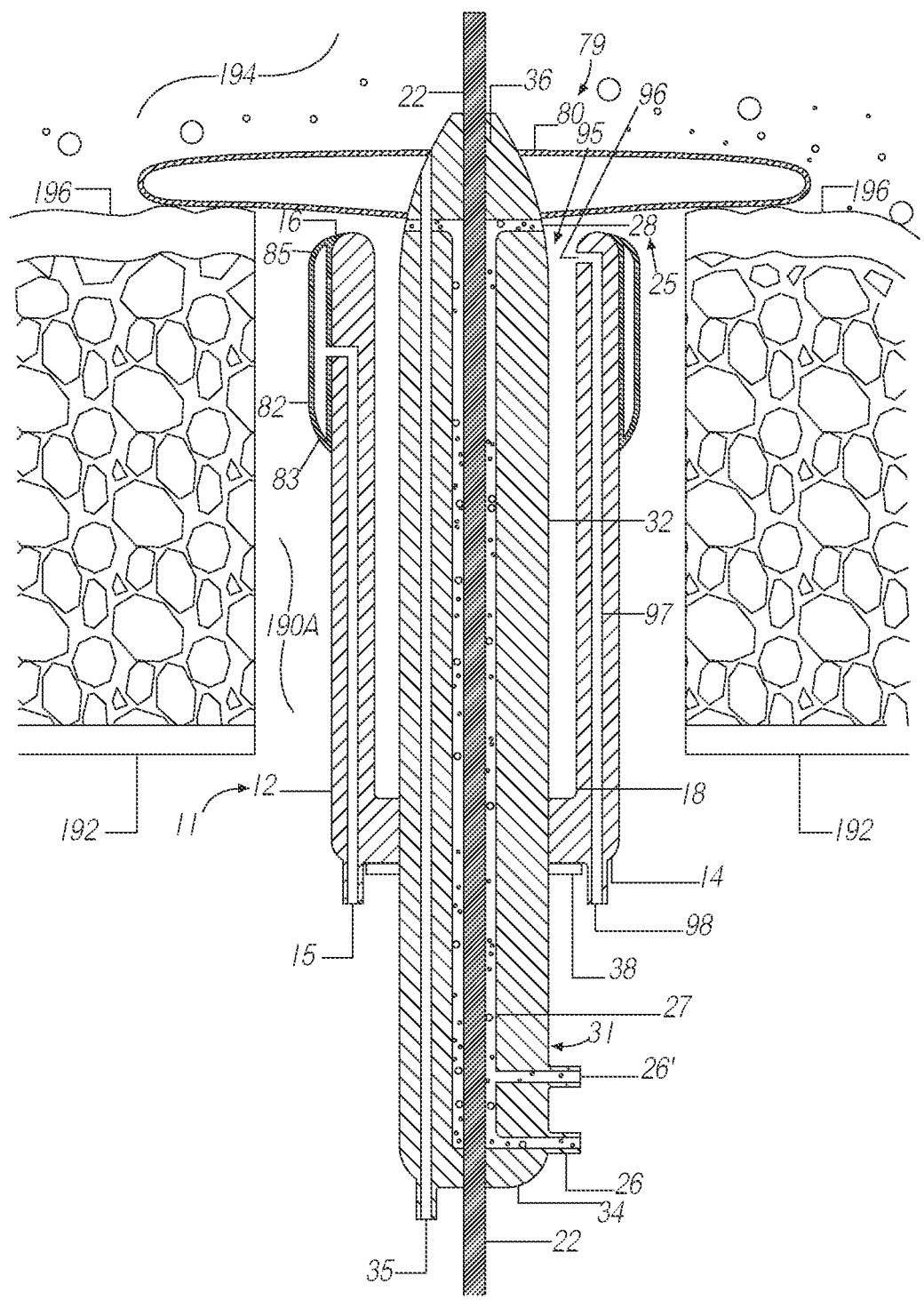
FIG. 23 is a schematic sectional representation of the embodiment of FIG. 22 in use showing an anchor balloon inflated and an anchor catheter/introducer occluding a puncture.
Figure 24:
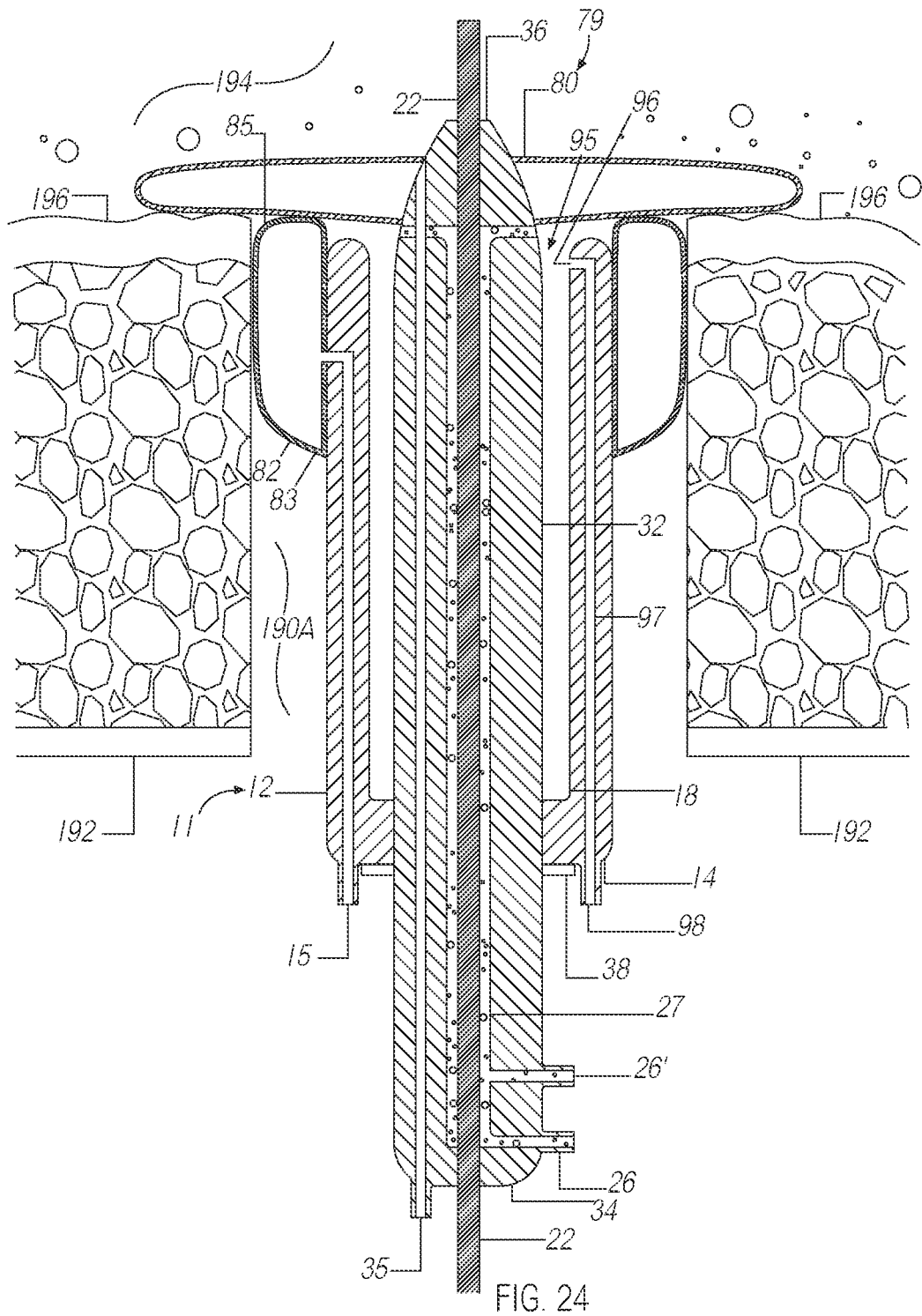
FIG. 24 is a schematic sectional representation of the embodiment of FIG. 22 in use showing an inflated occlusion balloon.

As shown in FIGS. 22, 23, and 24, the initial manner of operation of the puncture sealing system 10 of this embodiment is similar to the initial steps shown in FIGS. 3-6 discussed above. However, as can be seen in FIG. 24, when inflated, the occlusion balloon 82 does not wrap around the distal end 16 of the occlusion catheter 12 and thus the inflated occlusion balloon distal end 85 extends across a smaller portion of the puncture 190. The inflated occlusion balloon distal end 85 extends to or slightly beyond the distal end 16 in the distal direction extends inwardly towards the center of the occlusion catheter 12 to a lesser extent than the FIGS. 3-12 embodiment and in the version shown does not extend inwardly at all. An additional difference between the FIGS. 22-28 embodiment and the FIGS. 3-12 embodiment is the positioning of the one or more distal holes 28 of the vessel locator system 25. In this version, the one or more distal holes 28 are located within about 3 mm of the anchor balloon proximal end 84 and in one version are located within about 1 mm of the anchor balloon proximal end 84. This reduced distance allows for more precise positioning of the anchor balloon 80 in proximity to the arterial wall 196. This provides an improved double-detection mechanism for assuring proper positioning of the anchor catheter 32 with the anchor balloon 80 against the arterial wall 196 providing the operator with a feeling of slight resistance at the same time that blood flow through the vessel locator system 25 is abruptly terminated. Also, as shown in FIGS. 22-28 vessel locator proximal hole 26 is accompanied by a vessel locator port 26'. The vessel locator hole 26 and the vessel locator port 26' operate differently. The vessel locator hole 26 allows spontaneous flow to emanate if the puncture sealing system 10 is being used in an artery that's under pressure, while the vessel locator port 26' is a port that requires aspiration of blood with a syringe if the puncture sealing system 10 is being used in a vein that's not under high pressure. Also, as illustrated in FIGS. 22-24, the puncture sealing system 10 of this version can ensure that the occlusion balloon distal end 85 is positioned precisely within the vessel wall to enable occlusion and prevent blood from leaking into the surrounding tissue. To accomplish this, the occlusion catheter distal end 16 needs to be positioned just proximal and adjacent to the distal vessel locator hole 28, and the anchor catheter 32 and occlusion catheter 12 can be locked in this position as a unit by hub connector 38. By locking puncture sealing system 10 in this position, once the anchor catheter 32 is properly positioned, the occlusion balloon 82 can be inflated without any distal advancement of occlusion catheter 12 needed. In some circumstances, it may be needed to lock the anchor catheter 32 and the occlusion catheter 12 with the distal tip of the occlusion catheter 12 positioned more proximally, such as when it is desirable to not have the occlusion catheter 12 pass through the puncture 190. In this case, after the double detection mechanism positions the anchor catheter 32, then the anchor catheter 32 is stabilized and the occlusion catheter 12 is advanced distally to a hard stop to achieve the desired occlusion balloon position.

Figure 25:
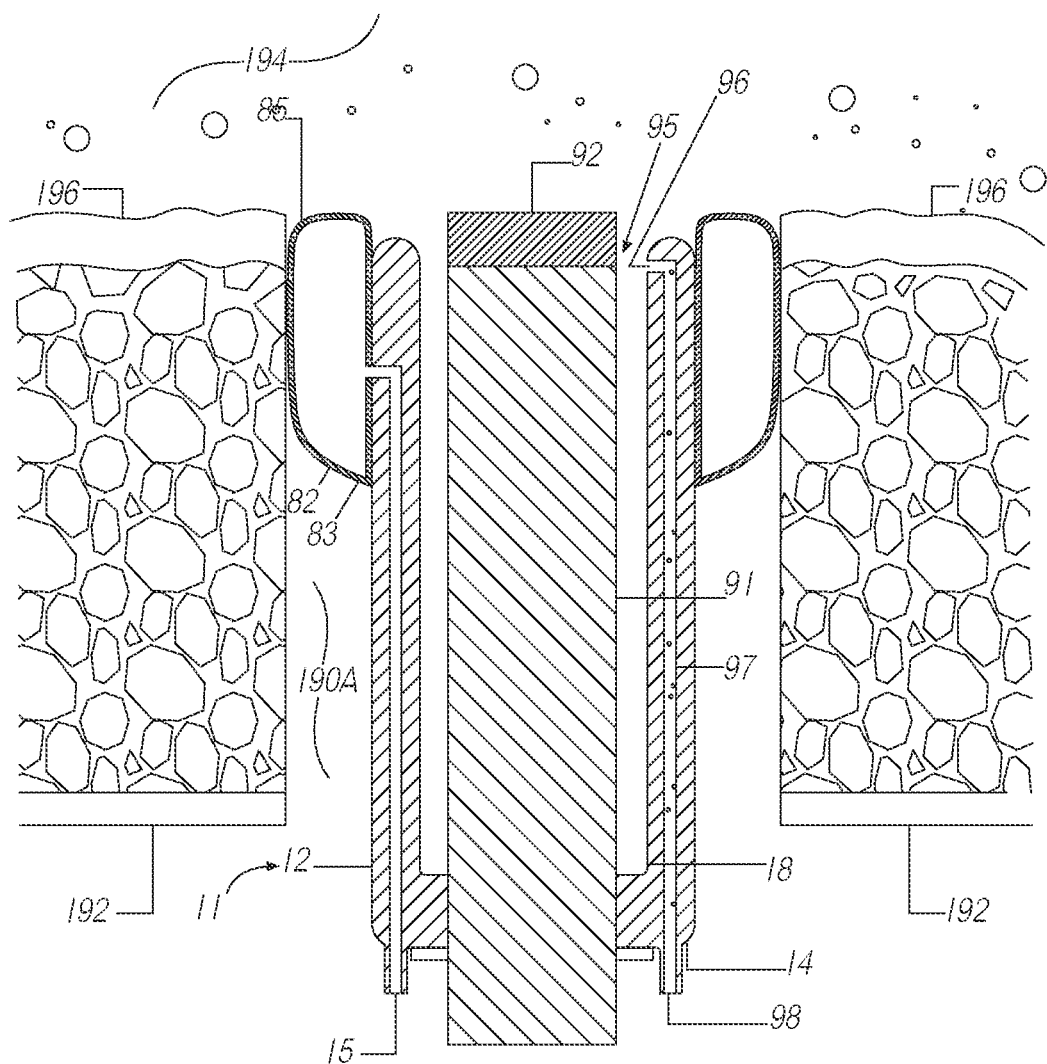
FIG. 25 is a schematic sectional representation of the embodiment of FIG. 22 in use showing the anchor catheter removed and replaced by an obturator.
Figure 26:
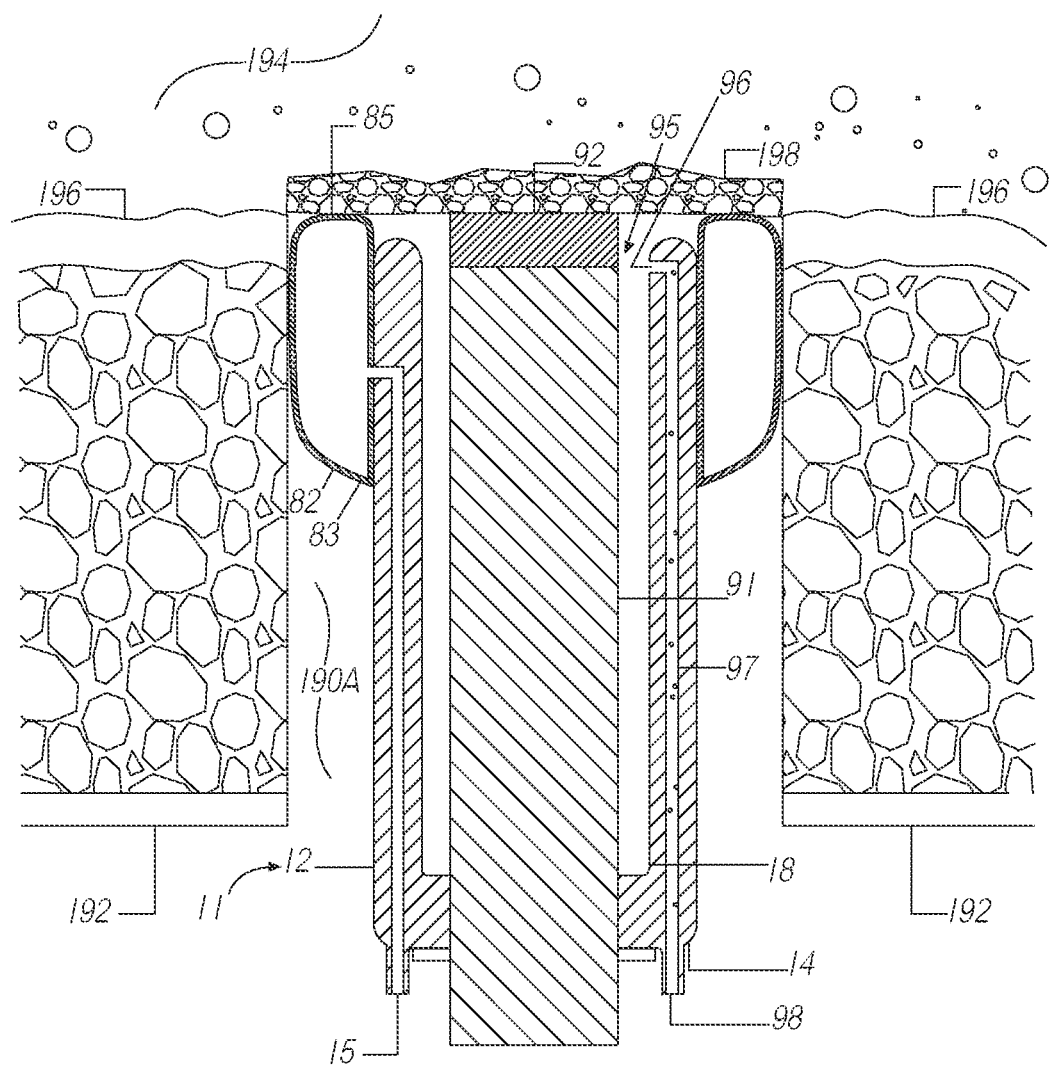
FIG. 26 is a schematic sectional representation of the embodiment of FIG. 22 in use showing the obturator helping to seal the puncture.

Referring now to FIGS. 24-26, the puncture sealing process of the embodiment of FIGS. 22-28 involves the deflation of the anchor balloon 80 and removal of the anchor catheter 32 prior to the puncture 190 being sealed. FIG. 25. shows the anchor catheter 32 removed and replaced by an obturator 91. The obturator 91 is a solid but flexible catheter that may be made of a similar material as the anchor catheter 32 and is sized, shaped, and configured to be insertable within the occlusion catheter lumen 18. The obturator 91 is sufficiently long that a distal end 92 can extend to or just beyond the occlusion catheter distal end 16. In this position, the distal end 92 of the obturator 91 operates in conjunction with the occlusion balloon distal end 85 to enable sealing or occlusion of the puncture 190, as shown in FIG. 26. The distal end 92 has a surface adapted to cover the puncture 190 in a region not covered by the inflated occlusion balloon 82 to enable the occlusion of the puncture. The surface may be adapted to cover substantially the entire puncture 190 or may be adapted to cover a portion of the puncture 190, such as a central portion within a portion that is covered by the inflated occlusion balloon 82. Once the puncture 190 and puncture tract 190A is sealed, the occlusion balloon 82 can be deflated and the puncture sealing system 10 can be removed from the area of the puncture tract 190A.

Optionally, the obturator distal end 92 can be configured to help facilitate hemostasis. For example, in one version, the obturator distal end 92 can be an expandable member so that when in position, the distal end 92 can expand to cover a larger portion of the puncture 190. The expandable member can be self-expanding, such as by being made of shape memory material, or can be inflatable like a balloon. In another version, the obturator distal end 92 can be composed of liquid silicone rubber or the like. The obturator distal end 92 and/or the occlusion balloon 82 may be coated with a procoagulant material, such as Chitosan, to enhance coagulation and hemostasis.

Figure 27:
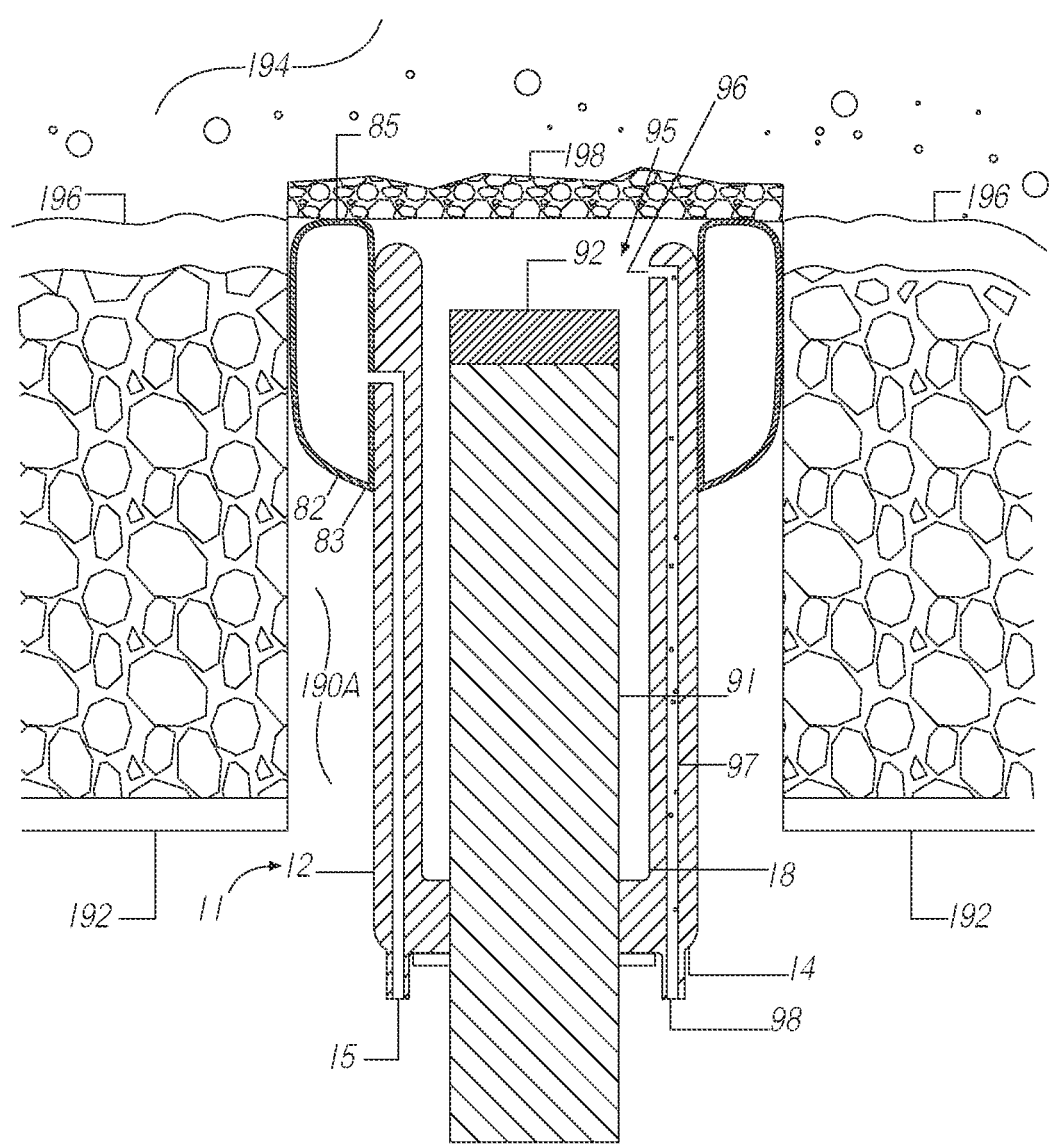
FIG. 27 is a schematic sectional representation of the embodiment of FIG. 22 in use showing the obturator moved proximally away from the puncture.
Figure 28:
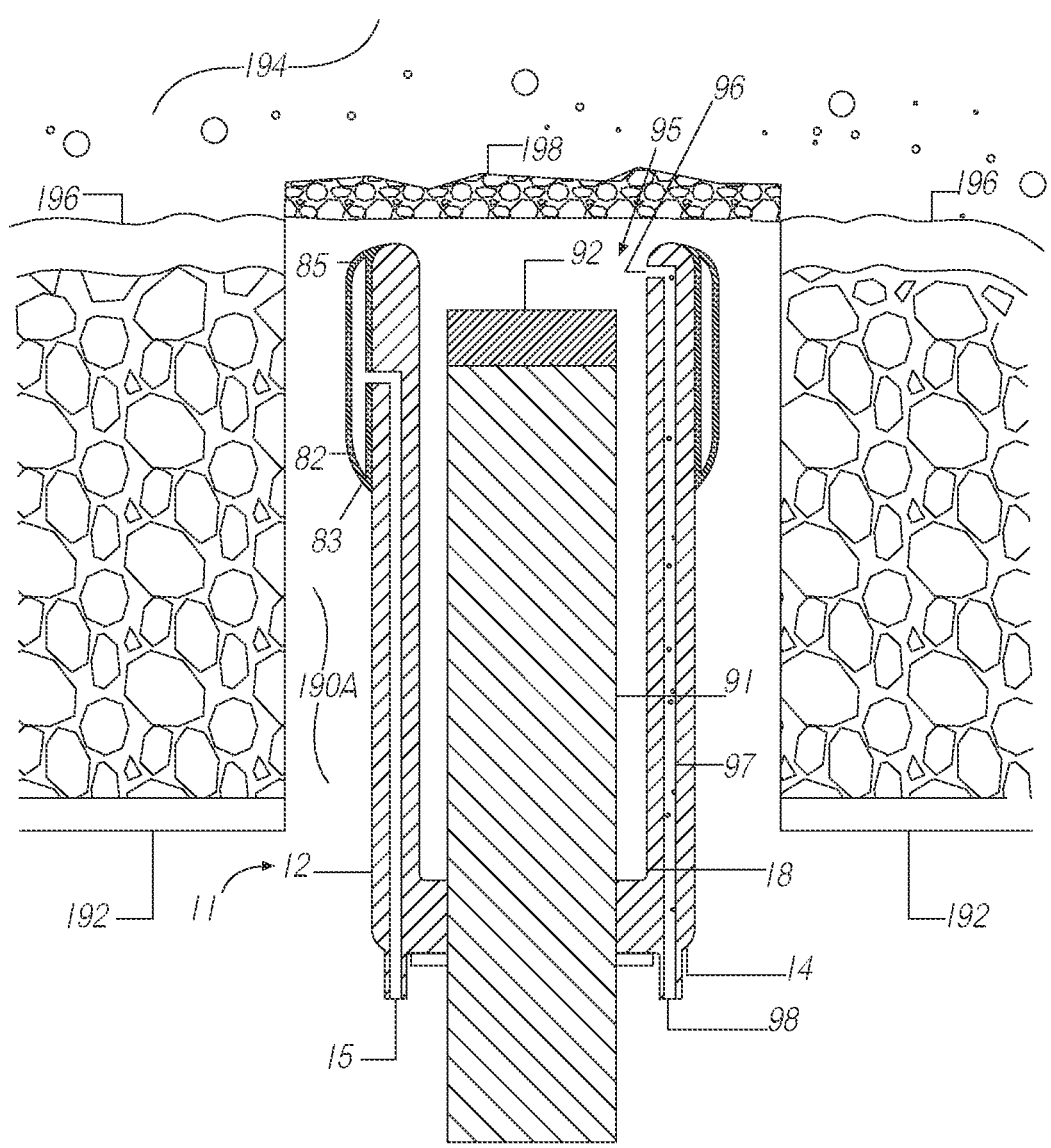
FIG. 28 is a schematic sectional representation of the embodiment of FIG. 22 in use showing occlusion balloon deflated.

The embodiment of FIGS. 22-28 also may include a hemostasis detection system 95. The hemostasis detection system 95 comprises an opening 96 into the occlusion catheter lumen 18 at the distal end 16 of the occlusion catheter 12. A hemostasis detection system lumen 97 communicates the opening 96 with a hemostasis detection system port 98 at the occlusion catheter proximal end 14. As shown in FIG. 27, to detect the level of hemostasis that has occurred, the obturator 91 can be moved proximally and slightly away from the puncture 190. If hemostasis is not complete, there will be blood present within the occlusion catheter lumen 18. By applying aspiration to the port 98, any such blood can be detected as it passes through the opening 96 and travels down the lumen 97. If, on the other hand, hemostasis in complete, the aspiration process will reveal little or no blood.

Figure 29:
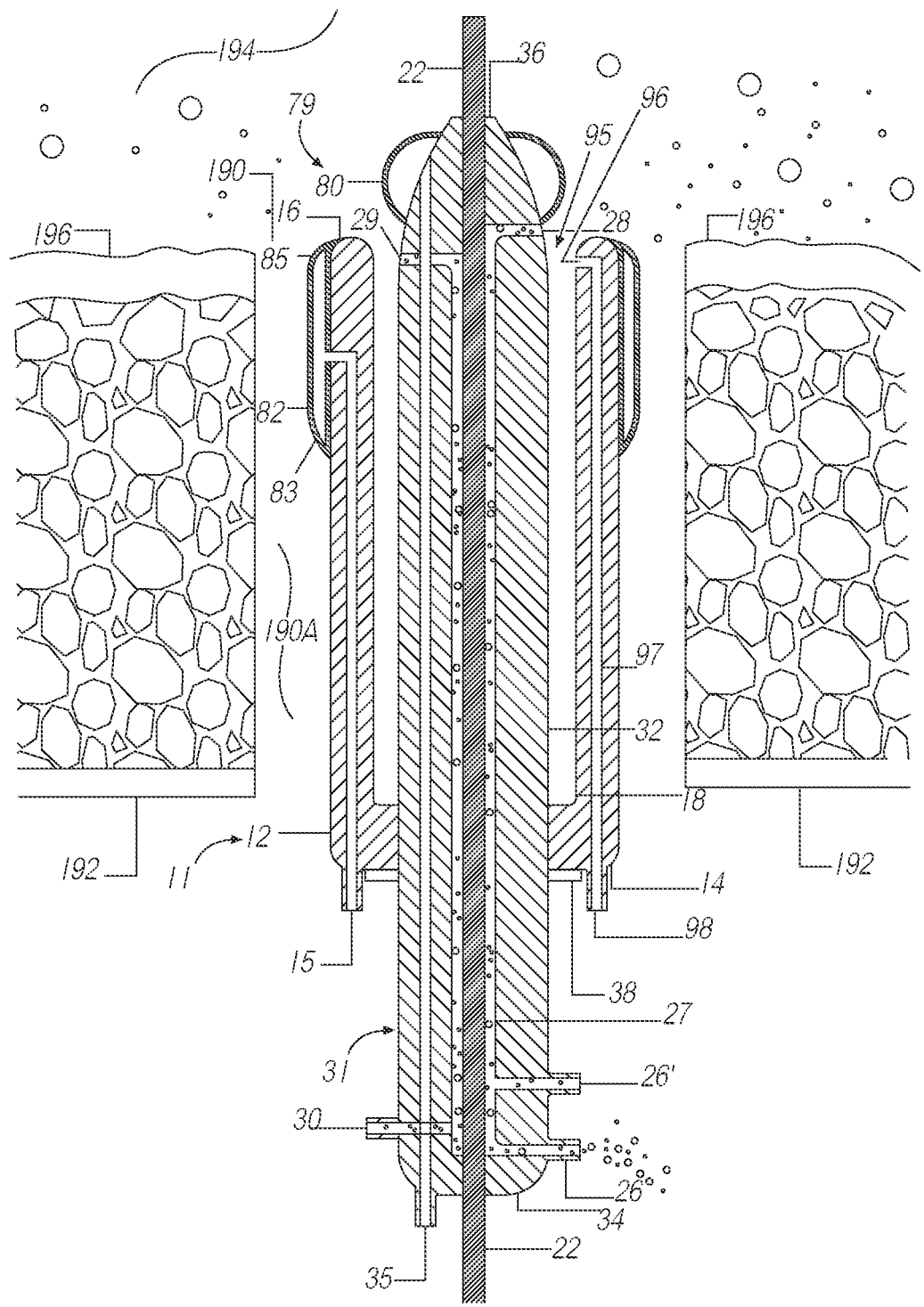
FIG. 29 is a schematic sectional representation of another embodiment of a puncture sealing system in accordance with the present invention.

FIG. 29 shows another embodiment of a puncture sealing system 10 according to the invention. The embodiment of FIG. 29 is similar to the version shown in connection with FIGS. 22-28. However, in the embodiment of FIG. 29, the vessel locator system 25 includes one or more second distal holes 29 that communicate with one or more second proximal holes 30. The one or more second distal holes 29 are located at a position proximally spaced from the one or more distal holes 28. The one or more distal holes 28 and the one or more second distal holes 29 provide an alternative method for assuring proper positioning of the anchor catheter 32. Initially the anchor catheter 32 is advanced distally with distal hole 28 and second distal hole 29 both entering the blood vessel lumen 194 at which point blood is detected emanating from proximal hole 26 and second proximal hole 30. As the anchor catheter 32 is retracted proximally, second distal hole 29 will exit the blood vessel lumen 194 and blood will abruptly stop emanating from second proximal hole 30, while distal hole 28 remains in the blood vessel lumen 194, and blood is still emanating from proximal hole 26. This is the desired position for anchor catheter 32. If anchor catheter 32 is retracted more proximally, then blood flow will abruptly stop emanating from both proximal hole 26 and second proximal hole 30, which indicates that the operator has pulled back too far. In one version the second distal holes 29 are separated proximally from the distal holes by from about 0.25 mm to about 3 mm, and in one version from about 0.25 mm to about 1 mm.

Figure 30:
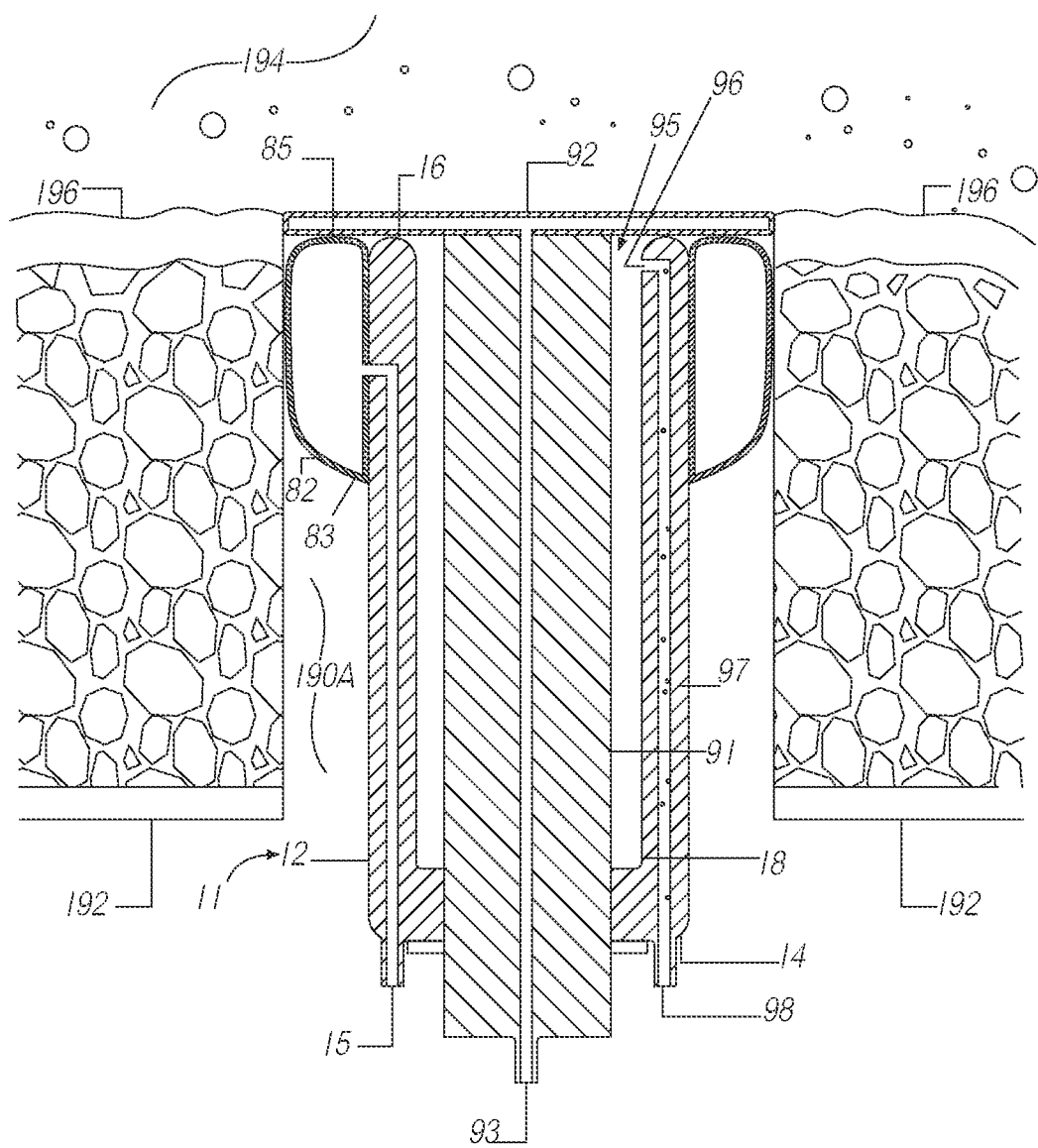
FIG. 30 is a schematic sectional representation of another embodiment of a puncture sealing system in accordance with the present invention.

FIG. 30 shows another embodiment of a puncture sealing system 10 according to the invention. The embodiment of FIG. 30 is similar to the version shown in connection with FIGS. 22-28. However, in the embodiment of FIG. 30, the occlusion balloon distal end 85 does not extend beyond the occlusion catheter distal end 16 and does not contact the space of the puncture 190. Instead, the obturator 91 includes an expandable distal end 92 that expands outside the occlusion catheter 12 to cover the entire or nearly the entire puncture 190. An inflation lumen 93 can be provided in the obturator 91 for inflation of the expandable distal end 91. Use of a medical foam that is compressed while it passes through the occlusion catheter lumen but expands towards its uncompressed size after exiting the occlusion catheter lumen distally is another alternative.

Another embodiment, not shown, that may be used as a possible closure device in more superficial blood vessels, e.g., the radial artery, may use the above-described dilator/introducer with more than one distal vessel locator, to position the closure device in the arterial lumen. The puncture tract of the radial artery is very short and may only accommodate a very short occlusion balloon, which may not be an effective way of stabilizing the closure device in the puncture tract. It may be preferable to use a different expandable member around the occlusion catheter, e.g., a medical foam, that may extend along a length of the occlusion catheter and may provide a frictional interface for stabilizing the closure device in the puncture tract. A circumferential compressive wrist band using velcro, may be needed along with or in place of the occlusion catheter expandable member, to stabilize the closure device in the puncture tract. This closure device may similarly use an obturator with expandable member, to completely seal the puncture and the distal puncture tract.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Throughout this specification and any claims appended hereto, unless the context makes it clear otherwise, the term "comprise" and its variations such as "comprises" and "comprising" should be understood to imply the inclusion of a stated element, limitation, or step but not the exclusion of any other elements, limitations, or steps. Therefore, any appended claims should not be limited to the description of the preferred versions contained herein and should include all such alterations, permutations, and equivalents as fall within the true spirit and scope of the present invention.

What is claimed is:

1. A puncture sealing system for sealing a vascular puncture, the system comprising:
   an inner member comprising an expandable member at an inner member distal end and an inflation lumen that extends from an inner member proximal end to an interior of the expandable member, wherein the inner member further comprises a vessel locator system comprising a lumen extending from one or more vessel locator distal holes to a vessel locator proximal hole, wherein the one or more vessel locator distal holes are positioned on the inner member proximal to the expandable member and within about 3 mm of the expandable member; and
   an outer member comprising a lumen sized and shaped to allow the inner member to slide therein, an occlusion balloon at an outer member distal end, and an inflation lumen that extends from an outer member proximal end to the interior of the occlusion balloon,
   wherein the expandable member can be inflated by fluid flowing through the inner member inflation lumen so that the expandable member can inflate in a subcutaneous vessel of a living being, and wherein the occlusion balloon can be inflated by fluid flowing through the outer member inflation lumen so that the occlusion balloon can apply pressure to at least a puncture tract extending from the vascular puncture.

2. A system according to claim 1 wherein the vessel locator system allows for back-bleeding from the vessel to provide a perceptible signal indicative of the location of the inner member with respect to the vessel.

3. A system according to claim 1 wherein the one or more vessel locator distal holes are positioned on the inner member proximal to the expandable member.

4. A system according to claim 1 wherein the vessel locator system further comprises one or more second distal locator holes spaced proximally from the one or more vessel locator distal holes.

5. A system according to claim 1 further comprising a vessel locator port wherein the vessel locator proximal hole allows spontaneous flow to emanate when the puncture sealing system is being used in an artery that's under pressure, and wherein the vessel locator port can be aspirated to locate positioning when the puncture sealing system is being used in a vein.

6. A system according to claim 1 wherein the system comprises a hub connector that biases the inner member relative to the outer member.

7. A system according to claim 1 wherein the inner member is an anchor catheter or a dilator catheter.

8. A system according to claim 1 wherein the inner member is removeable from the outer member while the occlusion balloon is inflated and wherein the occlusion balloon can then enable the occlusion of the puncture.

9. A system according to claim 8 wherein the occlusion balloon when inflated extends beyond and wraps around a distal end of the outer member so that the occlusion balloon can cover at least a portion of the puncture in addition to contacting and applying pressure to the puncture tract.

10. A system according to claim 8 wherein the occlusion balloon does not wrap around a distal end of the outer member and covers less than the entire puncture when inflated.

11. A system according to claim 8 further comprising an obturator slidably receivable within the outer member after the inner member has been removed from the outer member.

12. A system according to claim 11 wherein the obturator comprises a distal end having a surface adapted to cover the puncture in a region not covered by the inflated occlusion balloon to enable the occlusion of the puncture.

13. A system according to claim 12 wherein the obturator distal end comprises an expandable member.

14. A system according to claim 12 wherein the obturator distal end has at least one surface coated with a procoagulant material to enhance coagulation and hemostasis.

15. A puncture sealing system for sealing a vascular puncture, the system comprising:
    an inner catheter system comprising a first catheter comprising a vessel locator system and a second catheter comprising an expandable member, wherein the vessel locator system comprises a lumen extending from one or more vessel locator distal holes in the first catheter to a vessel locator proximal hole in the first catheter;
    an outer member comprising a lumen sized and shaped to receive the inner catheter system therein, an occlusion balloon at an outer member distal end, and an inflation lumen that extends from an outer member proximal end to the interior of the occlusion balloon; and
    an obturator slidably receivable within the outer member following removal of the inner catheter system from the outer member, the obturator comprising a distal end positionable in proximity to the vascular puncture,
    wherein the first catheter of the inner catheter system can be positioned within a vessel having a puncture, wherein the position of the first catheter of the inner catheter system within the vessel can be determined by back-bleeding from the vessel through the vessel locator system to provide a perceptible signal indicative of the location of the first catheter of the inner catheter system with respect to the vessel, wherein the second catheter can then be inserted within the outer member so the expandable member can be inflated, wherein the occlusion balloon can then be inflated by fluid flowing through the outer member inflation lumen so that the occlusion balloon can contact and apply pressure to at least a puncture tract extending from the vascular puncture, and wherein the obturator can then be received within the outer member following removal of the inner catheter system from the outer member so that the distal end of the obturator covers at least a portion of the vascular puncture to enable occlusion of the vascular puncture.

16. A puncture sealing system according to claim 15 wherein the occlusion balloon when inflated also contacts and covers a portion of the vascular puncture so that the occlusion balloon in combination with the obturator distal end enable occlusion of the vascular puncture.

17. A puncture sealing system according to claim 15 wherein the obturator distal end is expandable.

18. A puncture sealing system according to claim 15 wherein the second catheter is insertable after insertion of the first catheter.

19. A puncture sealing system according to claim 15 wherein the second catheter is advanceable within a lumen of the first catheter.

20. A puncture sealing system for sealing a vascular puncture, the system comprising:
- an inner member comprising a vessel locator system comprising a lumen extending from one or more vessel locator distal holes to a vessel locator proximal hole;
- an outer member comprising a lumen sized and shaped to allow the inner member to slide therein, an occlusion balloon at an outer member distal end, and an inflation lumen that extends from an outer member proximal end to the interior of the occlusion balloon; and
- an obturator slidably receivable within the outer member following removal of the inner member from the outer member, the obturator comprising a distal end positionable in proximity to the vascular puncture,
- wherein the inner member can be positioned within a vessel having a puncture, wherein the position of the inner member within the vessel can be determined by back-bleeding from the vessel through the vessel locator system to provide a perceptible signal indicative of the location of the inner member with respect to the vessel, wherein the occlusion balloon can then be inflated by fluid flowing through the outer member inflation lumen so that the occlusion balloon can contact and apply pressure to at least a puncture tract extending from the vascular puncture, wherein the inner member can be removed from the outer member, wherein the obturator can then be received within the outer member so that the distal end covers at least a portion of the vascular puncture to enable occlusion of the vascular puncture, wherein the inner member is an inner catheter system comprising a first catheter comprising the vessel locator system and a second catheter comprising an expandable member, and wherein the second catheter is advanceable within a lumen of the first catheter.

* * * * *